(12) United States Patent
Spiegelman

(10) Patent No.: US 7,691,578 B2
(45) Date of Patent: Apr. 6, 2010

(54) METHODS AND COMPOSITIONS FOR TREATING OBESITY

(75) Inventor: Bruce M. Spiegelman, Waban, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 11/571,714

(22) PCT Filed: Jul. 7, 2005

(86) PCT No.: PCT/US2005/024064

§ 371 (c)(1),
(2), (4) Date: Sep. 4, 2007

(87) PCT Pub. No.: WO2006/014529

PCT Pub. Date: Feb. 9, 2006

(65) Prior Publication Data

US 2008/0262093 A1    Oct. 23, 2008

Related U.S. Application Data

(60) Provisional application No. 60/586,359, filed on Jul. 7, 2004.

(51) Int. Cl.
  C12Q 1/68     (2006.01)
  C12Q 1/00     (2006.01)
  G01N 33/53    (2006.01)
(52) U.S. Cl. .................... 435/6; 435/7.1; 435/7.21
(58) Field of Classification Search ............. None
See application file for complete search history.

(56) References Cited

U.S. PATENT DOCUMENTS

| 4,724,234 | A | 2/1988 | Cone, Jr. |
| 5,741,666 | A | 4/1998 | Tartaglia |
| 5,853,975 | A | 12/1998 | Tartaglia |
| 6,166,192 | A | 12/2000 | Spiegelman et al. |
| 6,197,530 | B1 | 3/2001 | Stricker-Krongrad et al. |
| 6,218,122 | B1 | 4/2001 | Friend et al. |
| 6,403,784 | B1 | 6/2002 | Turner, Jr. et al. |
| 7,091,006 | B2 | 8/2006 | Spiegelman et al. |
| 7,250,283 | B2 | 7/2007 | Spiegelman et al. |

FOREIGN PATENT DOCUMENTS

| WO | WO-98/54220 | 12/1998 |
| WO | WO-00/32215 | 6/2000 |
| WO | WO-2004/041256 | 5/2004 |

OTHER PUBLICATIONS

Castillo et al., "An adipogenic cofactor bound by the differentiation domain of PPARγ," The EMBO Journal, 18(13):3676-3687 (1999).
Chirgwin et al., "Isolation of biologically active ribonucleic acid from sources enriched in ribonuclease," Biochemistry, 18:5294-5299 (1979).
Emilsson, V. et al., "The effects of rexinoids and rosiglitazone on body weight and uncoupling protein isoform expression in the Zucker fa/fa rat," Metabolism 49(12):1610-1615 (2000).
Erlanson-Albertsson C., "The role of uncoupling proteins in the regulation of metabolism," Acta Physiol Scand. 178(4):405-412 (2003).
Fleury C. et al., "Uncoupling protein-2: a novel gene linked to obesity and hyperinsulinemia," Nature Genetics Mar;15(3):269-72 (1998).
GenBank Accession No. AF453324.
GenBank Accession No. AAL47054.
Grundy, S.M. & Barnett, J.P., "Metabolic and health complications of obesity," Dis. Mon. 36:641-731 (1990).
Harper, J.A. et al., "Mitochondrial uncoupling as a target for drug development for the treatment of obesity," Obes. Rev. 2(4):255-265 (2001).
Herzig, S. et al., "CREB regulates hepatic gluconeogenesis through the coactivator PGC-1," Nature 413:179-183 (2001).
Huang, S-G., "Development of a high throughput screening assay for mitochondrial membrane potential in living cells," J. Biomol. Screen. 7(4):383-389 (2002).
Jucker et al., "Assessment of mitochondrial energy coupling in vivo by $^{13}C/^{31}P$ NMR," Proc. Natl. Acad. Sci. USA 97:6880-6884 (2000).
Kakuma et al., "Role of leptin in peroxisome-proliferator-activated receptor gamma coactivator-1 expression," Endocrinology 141(12):4576-4582 (2000).
Kurt, T.L. et al., "Dinitrophenol in weight loss: the poison center and public health safety," Vet. Hum. Toxicol. 28(6):574-575 (1986).
Larrouy, D. et al., "Cloning and mRNA tissue distribution of human PPARγ coactivator-1," Int. J. Obes. 23:1327-1332 (1999).
Lehman, J.J. et al., "Peroxisome proliferator-activated receptor γ coactivator-1 promotes cardiac mitochondrial biogenesis," J. Clin. Invest. 106:847-856 (2000).
Lin, J. et al., "Peroxisome Proliferator-activated Receptor γ Coactivator 1β (PGC-1β, A Novel PGC-1-related Transcription Coactivator Associated with Host Cell Factor," Journal Biol. Chem. 277(3):1645-1648 (2002).
Michael, L.F. et al., "Restoration of insulin-sensitive glucose transporter (GLUT4) gene expression in muscle cells by the transcriptional coactivator PGC-1," Proc. Natl. Acad. Sci. USA 98:3820-3825 (2001).
Nishina, P.M. et al., "Atherosclerosis in Genetically Obese Mice: The Mutants Obese, Diabetes, Fat, Tubby, and Lethal Yellow," Metab. 43:554-558 (1994).
Parascandola, J., "Dinitrophenol and bioenergetics: an historical perspective," Molecular and Cellular Biochemistry 5(1-2):69-77 (1974).
Puigserver, P. et al., "A cold-inducible coactivator of nuclear receptors linked to adaptive thermogenesis," Cell 92(6):829-839 (1998).
Rossmeisl, M. et al., "Expression fo the uncoupling protein 1 from the aP2 gene promoter stimulates mitochondrial biogenesis in unilocular adipocytes in vivo," Eur. J. Biochem. 269:19-28 (2002).

(Continued)

Primary Examiner—James Martinell
(74) Attorney, Agent, or Firm—Foley Hoag, LLP

(57) ABSTRACT

The present invention relates to therapeutic compositions for treating or preventing obesity and obesity-related disorders in a subject. The present invention also relates to the use of PGC-1 expression levels to determine the safe dosage range for known or putative respiration uncoupling agents for use as anti-obesity therapeutics. The present invention further relates to methods for identifying new compounds that have respiration uncoupling activity.

41 Claims, 13 Drawing Sheets

OTHER PUBLICATIONS

Sears, I. B. et al., "Differentiation-Dependent Expression of the Brown Adipocyte Uncoupling Protein Gene: Regulation by Peroxisome Proliferator-Activated Receptor γ," Mol. Cell. Biol. 16(7):3410-3419 (1996).

Simkins, S., "Dinitrophenol and Desiccated Thyroid in the Treatment of Obesity," Journal A.M.A., 108(25):2110-2117 (1937).

Tainter, M.L. et al., "Use of Dinitrophenol in Nutritional Disorders," Am. J. Public Health Nations Health 24(10):1045-1053 (1934).

Vega, R.B. et al., "The Coactivator PGC-1 Cooperates with Peroxisome Proliferator-Activated Receptor α in Transcriptional Control of Nuclear Genes Encoding Mitochondrial Fatty Acid Oxidation Enzymes," Mol. Cell. Biol. 20:1868-1876 (2000).

Wangsness, M., "Pharmacological treatment of obesity," Minn. Med. 83(11):21-26 (2000).

Wu, Z. et al., "Mechanisms Controlling Mitochondrial Biogenesis and Respiration through the Thermogenic Coactivator PGC-1," Cell 98:115-124 (1999).

Yoon J.C. et al. "Control of hepatic gluconeogenesis through the transcriptional coactivator PGC-1," Nature 413(6852):131-138 (2001).

Bekele et al., "A Bayesian Approach to Jointly Modeling Toxicity and Biomarker Expression in a Phase I/II Dose-Finding Trial," Biometrics, 61(2):344-354 (2005).

Rolan, Paul, "The contribution of clinical pharmacology surrogates and models to drug development—a critical appraisal," British Journal of Clinical Pharmacology, 44(3):219-225 (1997).

Rolan et al., "Use of biomarkers from drug discovery through clinical practice: Report of the Ninth European Federation of Pharmaceutical Sciences Conference on Optimizing Drug Development," Clinical Pharmacology & Therapeutics, 73(4):284-291 (2003).

Tsuboyama-Kasaoka et al., "Low Level Overexpression of UCP2 in Adipose Tissues Up-Regulates PGC-1 and Ameliorates High Fat Diet-Induced Obesity and Metabolic Abnormalities," International Journal of Obesity, 26:S23 Abstract (2002).

Supplementary European Search Report dated Apr. 4, 2008.

Figure 5
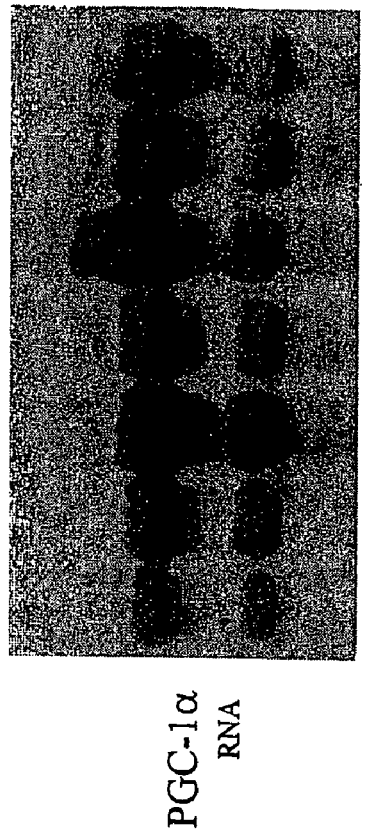
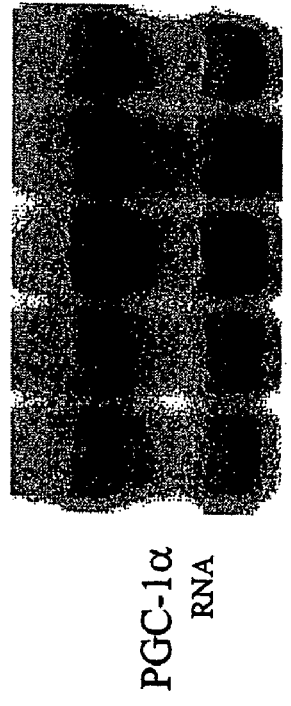

Figure 6
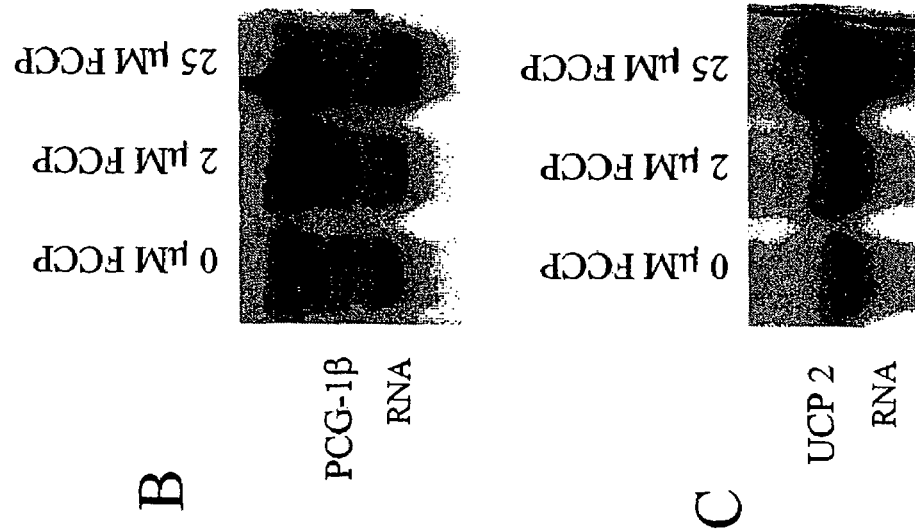
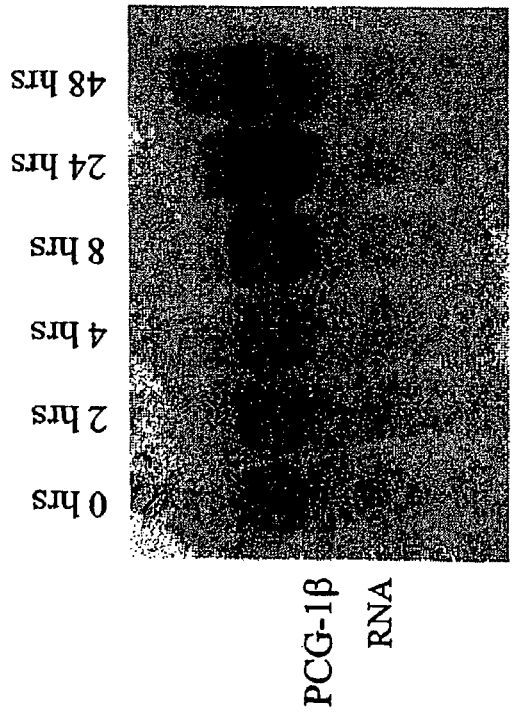

A  PCG-1α RNA

B  PCG-1β RNA

C  mtTFA RNA

METHODS AND COMPOSITIONS FOR TREATING OBESITY

RELATED APPLICATIONS

This application claims the benefit of U.S. Provisional Application No. 60/586,359, filed Jul. 7, 2004, the contents of which is specifically incorporated by reference herein in its entirety.

BACKGROUND OF THE INVENTION

Obesity represents the most prevalent of body weight disorders, affecting an estimated 30 to 50% of the middle-aged population in the western world. Obesity, defined as a body mass index (BMI) of 30 kg/$^2$m or more, contributes to diseases such as coronary artery disease, hypertension, stroke, diabetes, hyperlipidemia and some cancers. (See, e.g., Nishina, P. M. et al. (1994), *Metab.* 43:554-558; Grundy, S. M. & Barnett, J. P. (1990), Dis. Mon. 36:641-731). Obesity is a complex multifactorial chronic disease that develops from an interaction of genotype and the environment and involves social, behavioral, cultural, physiological, metabolic and genetic factors.

Generally, obesity results when energy intake exceeds energy expenditure, resulting in the growth and/or formation of adipose tissue via hypertrophic and hyperplastic growth. Hypertrophic growth is an increase in size of adipocytes stimulated by lipid accumulation. Hyperplastic growth is defined as an increase in the number of adipocytes in adipose tissue. It is thought to occur primarily by mitosis of pre-existing adipocytes caused when adipocytes fill with lipid and reach a critical size. An increase in the number of adipocytes has far-reaching consequences for the treatment and prevention of obesity.

Adipose tissue consists primarily of adipocytes. Vertebrates possess two distinct types of adipose tissue: white adipose tissue (WAT) and brown adipose tissue (BAT). WAT stores and releases fat according to the nutritional needs of the animal. This stored fat is used by the body for (1) heat insulation (e.g., subcutaneous fat), (2) mechanical cushion (e.g., surrounding internal organs), and (3) as a source of energy. BAT burns fat, releasing the energy as heat through thermogenesis. BAT thermogenesis is used both (1) to maintain homeothermy by increasing thermogenesis in response to lower temperatures and (2) to maintain energy balance by increasing energy expenditure in response to increases in caloric intake (Sears, I. B. et al. (1996) *Mol. Cell. Biol.* 16(7): 3410-3419). BAT is also the major site of thermogenesis in rodents and plays an important role in thermogenesis in human infants. In humans, and to a lesser extent rodents, brown fat diminishes with age, but can be re-activated under certain conditions, such as prolonged exposure to cold, maintenance on a high fat diet and in the presence of noradrenaline producing tumors.

Fat metabolism is regulated by two pathways, lipogenesis and lipolysis. Lipogenesis is the deposition of fat which occurs in the liver and in adipose tissue at cytoplasmic and mitochondrial sites. This process allows the storage of energy that is ingested which is not needed for current energy demands. Lipolysis is the chemical decomposition and release of fat from adipose and/or other tissues. This process predominates over lipogenesis when additional energy is required by the body.

Any treatment for obesity has to reduce energy intake, increase energy expenditure or combine both effects. Respiration uncoupling agents such as carbonyl cyanide p-trifluoro-methoxyphenylhydrazone ("FCCP") are well known in the art as having dramatic weight loss inducing effects. However, such agents are also associated with high mortality and serious side effects. The negative effects of such compounds are linked to the severe drop in ATP levels caused by excessively high doses of uncoupling agents.

Current therapies for obesity predominantly lead to decreased energy intake by acting at satiety centers in the brain or by reducing the efficiency of intestinal absorption. To date, no safe and reliable molecular mechanism for treating and/or preventing obesity by increasing energy expenditure or metabolic activity has been identified. Given the severity and prevalence of obesity related disorders, there exists a great need for the identification of an anti-obesity therapeutic.

SUMMARY OF THE INVENTION

The present invention is based, at least in part, on the discovery that the expression level of PGC-1, e.g., expression of PGC-1 protein or mRNA, can be used to determine a safe dosage range of a known or putative respiration uncoupling agent. In another aspect, the invention pertains to methods for discovering new compounds that have respiration uncoupling activity.

In one aspect, the present invention provides a method of identifying the upper limit of a safe dosage range for a respiration uncoupling agent comprising the steps of contacting a cell expressing PGC-1 with varying amounts of the respiration uncoupling agent, determining the maximum PGC-1 expression level and the corresponding amount of the respiration uncoupling agent, to thereby identify the upper limit of the safe dosage range for the respiration uncoupling agent.

In one embodiment, the upper limit of the safe dosage range of a respiration uncoupling agent is identified by the steps of contacting a cell expressing PGC-1 with varying amounts of the respiration uncoupling agent, determining the maximum PGC-1 expression level and the corresponding amount of the respiration uncoupling agent, to thereby identify the upper limit of the safe dosage range for the respiration uncoupling agent.

In another embodiment, a safe dosage range of the respiration uncoupling agent is identified. In another embodiment the safe dosage range of a respiration uncoupling agent is identified by the steps of contacting a cell expressing PGC-1 with varying amounts of the respiration uncoupling agent, determining the maximum PGC-1 expression level and the corresponding amount of the respiration uncoupling agent, to thereby identify the upper limit of the safe dosage range for the respiration uncoupling agent.

In one embodiment, a safe dosage range of a respiration uncoupling agent may be determined by, for example, determining the level of ATP, determining the level of lactic acid, determining the metabolic rate of the cell, or determining the level of AMP kinase.

In further embodiments of the methods of the invention, the determination of the maximum PGC-1 expression level is carried out by identifying whether the safe dosage is capable of decreasing fat mass, decreasing adipocity, or increasing weight loss in a subject.

In another aspect of the invention, a method for identifying a compound capable of respiration uncoupling activity is provided comprising the steps of contacting a cell expressing PGC-1 with a test compound, and assaying the ability of the test compound to stimulate the expression of PGC-1, thereby identifying a compound capable of respiration uncoupling activity.

In one embodiment, the respiration uncoupling agent is FCCP. In another embodiment the respiration uncoupling agent is selected from the group consisting of FCCP, DNP, and CCCP.

In one embodiment, the PGC-1 expression level is detected by an anti-PGC-1 antibody. In another embodiment, the PGC-1 expression level is detected by the PGC-1 mRNA level.

In one aspect, the invention provides a method for increasing metabolic activity of a cell comprising the steps of contacting the cell with a safe dose of a respiration uncoupling agent, wherein the safe dose of the respiration uncoupling agent is identified by contacting a cell expressing PGC-1 with varying amounts of the respiration uncoupling agent, determining the maximum PGC-1 expression level and the corresponding amount of the respiration uncoupling agent to thereby identify the upper limit of the safe dosage range for the respiration uncoupling agent.

In one embodiment, the cell is, for example, an adipocyte. In another embodiment, the cell is selected from the group consisting of adipose, muscle, and neural cells.

In another aspect of the invention, a method is provided for treating obesity or a obesity-related disorder in a subject comprising administering to the subject a safe dosage of a respiration uncoupling agent such that obesity or the obesity-related disorder is treated.

In one embodiment, the obesity related disorder is selected from the group consisting of obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia.

The respiration uncoupling agents of the invention can be administered to a subject, for example, intravenously, intraperitoneally, or orally.

In one aspect of the invention, a kit is provided for identifying the upper limit of a safe dosage range for a respiration uncoupling agent comprising a cell expressing PGC-1, an agent capable of determining the maximum PGC-1 expression levels, and instructions for use. In another aspect, the invention provides a kit for identifying a compound capable of respiration uncoupling activity comprising a cell expressing PGC-1, an agent capable of determining the maximum PGC-1 expression levels, and instructions for use.

Other features and advantages of the invention will be apparent from the following detailed description and claims.

BRIEF DESCRIPTION OF THE FIGURES

FIGS. 5A-5B are Northern blots illustrating that other mitochondrial inhibitors also cause PGC-1α expression levels to increase. (A) HIB1B brown fat cells treated with 10 μM Antimycin, a Complex III inhibitor, showed an increase in PGC-1α expression levels. (B) An increase in PGC-1α expression level was also observed after HIB1B cells were treated for 5 hours with 50 μM atractyloside (an inhibitor of the 20 adenine nucleotide transporter (ANT)) or 10 hours with 5 μM atractyloside.

FIGS. 6A-6C are Northern blots showing that FCCP causes an increase in expression of PGC-1β and its target gene UCP 2 in Fao liver hepatoma cells. (A) Fao cells were treated with 2 μM FCCP for 48 hours. Increased PGC-1β expression levels were observed after 24 hours of treatment. (B) Fao cells were treated with 2 and 25 μM FCCP for 24 hours. Both (b) PGC-1β and (C) UCP 2 expression levels were induced after treatment with 25 μM FCCP.

DETAILED DESCRIPTION OF THE INVENTION

Figure 1:
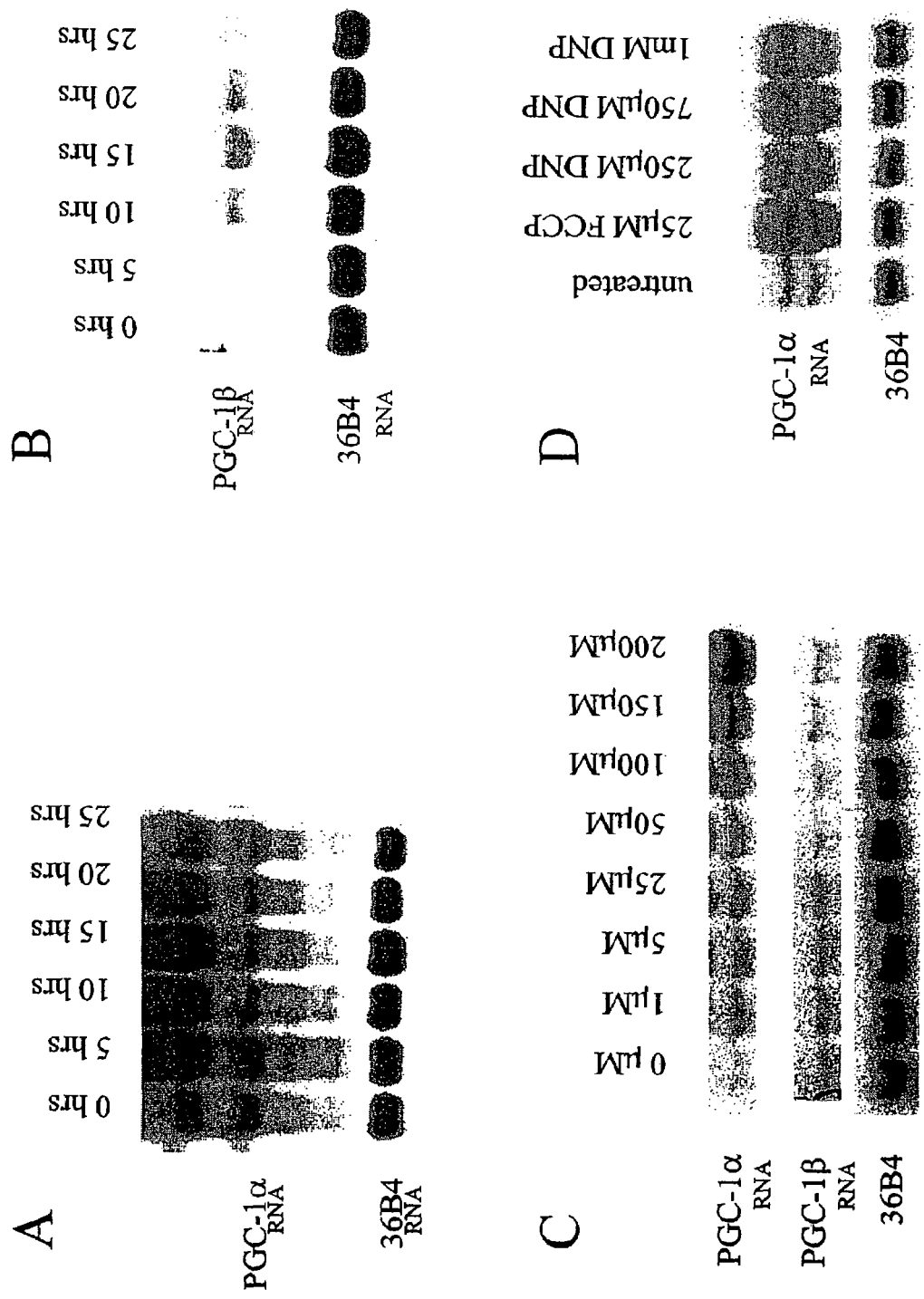
FIGS. 1A-1D are Northern blots depicting the induction of PGC-1α and PGC-1β expression in HIB1B brown fat cells as the result of mitochondrial stress caused by the uncoupling agent FCCP. (A) PGC-1α expression levels were induced after 5 hours of treatment with 25 μM FCCP. The increased PGC-1α levels were sustained for 20 additional hours. (B) PGC-1β expression levels were induced after 10-15 hours of treatment with 25 μM FCCP. PGC-1β levels remained induced until 25 hours of treatment. 36B4 expression levels serve as a loading control. (C) PGC-1α expression levels increase with increasing doses of FCCP whereas PGC-1β expression levels do not increase. Cells were treated for 5 hours. 36B4 is the loading control. (D) Like FCCP, dinitrophenol (DNP), another uncoupling agent, also causes an increase in PGC-1α expression. Cells were treated for 5 hours with three concentrations of DNP. Untreated cells and FCCP-treated cells serve as controls. 36B4 is the loading control.

The present invention is based, at least in part, on the discovery that decreasing the output of respiration leads to an increase in PGC-1 levels, e.g., PGC-1 expression or activity. The increased PGC-1 level functions to activate or stimulate an increased respiration activity that compensates for the loss of output of the respiration pathway. This feedback loop functions to maintain the ATP level in the body at a substantially constant level.

It has further been discovered that the expression level of PGC-1, which maintains ATP levels in the body, can be used to determine a safe and effective dosage range of a known or putative respiration uncoupling agent, e.g., FCCP. Once the PGC-1 expression level reaches a maximum level, i.e., PGC-1 expression levels stop increasing and remain substantially constant despite increasing levels of the respiration uncoupling agent, the PGC-1 present will not be able to compensate for the decline in ATP levels caused by the increasing levels of the respiration uncoupling agent. The time point at which maximum PGC-1 expression is achieved corresponds to the upper limit of a safe dosage range of the respiration uncoupling agent. PGC-1 expression levels may be determined by detecting levels of PGC-1 proteins by, e.g., a PGC-1 antibody-based assay known in the art and described herein. PGC-1 expression levels may also be determined by assaying PGC-1 nucleic acid, e.g., mRNA levels by, e.g., a PCR based assay known in the art and described herein.

Accordingly, the present invention provides methods for identifying safe and effective dosages of respiration uncoupling agents for administration to a subject to treat or prevent obesity or an obesity related disorder. In one embodiment, the safe and effective dosage of one or more respiration uncoupling agents is determined for a subject. In another embodiment, the safe and effective dosage is determined for a population of subjects, e.g., a population of subjects at risk for or suffering from obesity or an obesity related disorder. In addition to monitoring PGC-1 expression levels, several additional parameters may be analyzed to determine a safe and effective dosage range of a respiration uncoupling agent. For example, a safe dosage range of a respiration uncoupling agent may be further determined by measuring modulation of metabolic rate, e.g., increased metabolic rate; modulation of oxygen consumption, e.g., increased oxygen consumption; modulation of cellular respiration, e.g., increased cellular respiration; ATP levels; and/or body temperature. Furthermore, because glycolysis is accelerated during uncoupling, lactic acidosis also acts as a marker for respiration uncoupling and may be monitored to identify a safe dosage range of a respiration uncoupling agent. In addition, because protein kinase is decreased when PGC-1 is effectively compensating for the decline in ATP levels caused by increased levels of respiration uncoupling agent, it may also be used as a marker for respiration uncoupling. Accordingly, in one embodiment, a safe dosage range for a respiration uncoupling agent includes a dosage range at which PGC-1 levels and metabolic rate are increased, e.g., slightly increased, but body temperature and blood lactate levels are not increased.

An effective dosage range of a respiration uncoupling agent should also be a safe dosage range, and may also be determined by analysis of one or more indicators of respiration uncoupling, or the effects thereof. For example, an effective dosage range may be determined by monitoring weight change, e.g., weight loss; change in fat mass, e.g., loss of fat mass; change in the level of adiposity; modulation of metabolic rate, e.g., increased metabolic rate; modulation of oxygen consumption, e.g., increased oxygen consumption; modulation of cellular respiration, e.g., increased cellular respiration.

The present invention is further related to methods for discovering new compounds that have respiration uncoupling activity. Test compounds can be identified as respiration uncoupling agents by using the expression level of PGC-1 as a read-out, i.e., a respiration uncoupling agent would reduce respiration/ATP production resulting in a corresponding increase in PGC-1 expression levels. Safe and effective dosage ranges of compounds identified by the methods of the invention may also be determined using the methods described herein.

In order that the present invention may be more readily understood, certain terms are first defined. Additional definitions are set forth throughout the detailed description.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, including insulin resistant obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, "obesity" refers to a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" refers to reducing the BMI of the mammal to less than about 25.9, and maintaining that weight for a period of time, e.g., for at least about 6 months. The treatment suitably results in an increase in metabolic activity.

"Prevention" refers to preventing obesity or an obesity related disorder from occurring if the treatment is administered prior to the onset of the obese condition. Moreover, if treatment is commenced in subjects already suffering from or having symptoms of obesity or an obesity related disorder, such treatment is expected to prevent, or to prevent the progression of obesity or the obesity related disorder, and the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

As used herein, the term "respiration uncoupling agent" refers to any pharmacological agent that increases metabolic activity by increasing the uncoupling of mitochondrial oxidative phosphorylation. Mitochondria are normally responsible for 90% of cellular oxygen consumption and the majority of ATP production. The flow of electrons from reduced substrate to oxygen is coupled by a proton electrochemical gradient across the mitochondrial inner membrane to the synthesis of ATP from ADP and phosphate. This is the process of oxidative phosphorylation which can be divided into two distinct parts: the generation of the proton electrochemical gradient by the respiratory chain and the synthesis of ATP. However, not all of the energy is coupled to ATP synthesis. Instead much is lost by uncoupled reactions when protons leak, i.e., protons move from the cytosol back into the mitochondrial matrix via pathways that circumvent the ATP synthase and other uses of the electrochemical gradient. Proton cycling is a major contributor to the standard metabolic rate ("SMR") which refers to the minimum calorific requirement for normal life in an organism in the absence of external stimulation, work and growth. Stimulating proton leak, therefore, would result in more energy being dissipated during synthesis of ATP, an increase in the SMR and a corresponding reduction in obesity. Accordingly, in a preferred embodiment, a "respiration uncoupling agent" is any pharmacological agent that stimulates proton leak across the mitochondrial membrane. In another embodiment, a "respiration uncoupling agent" is any pharmacological agent that increases the SMR.

An exemplary respiration uncoupling agent is 2,4-dinitrophenol ("DNP"). DNP is a lipid-soluble weak acid which acts as a protonophore because it can cross membrane protonated, lose its proton and return as the anion, then reprotonate and repeat the cycle. Thus, DNP increases the proton conductance of mitochondria and functions as a respiration uncoupling agent. Although DNP was used with considerable success as an anti-obesity therapeutic in the 1930's, reports of severe side-effects, including death, led to its disuse (Simkins, S. (1937) *Journal A. M. A.* June 19:2110; Parascandola, J. (1974) *Molecular and Cellular Biochemistry* 5(1-2):69). In fact, although it was shown to promote direct stimulation of cellular respiration and a subsequent rise in body temperature in animals, large doses led to almost immediate onset of rigor mortis. Accordingly, to maximize the therapeutic potential of DNP and other known and putative respiration uncoupling agents, it is imperative to determine the safe dosage ranges, as provided by the methods of the present invention.

Other exemplary respiration uncoupling agents include, but are not limited to, FCCP and cyanide m-chloro-phenylhydrazone (CCCP).

As used herein, the term "PGC-1" refers to a PPARγ Coactivator 1 protein and is intended to include any of its' derivatives, including PGC-1α and PGC-1β. PGC-1 has been described previously (Puigserver, P. et al. (1998) *Cell* 92(6): 829-39; U.S. Pat. No. 6,166,192; and PCT International Publication Nos. WO 98/54220; the contents of all of which are incorporated herein by reference). The nucleic acid sequences of human PGC-1, PGC-1α and PGC-1β are provided herein as SEQ ID NOs: 1, 3, and 5, respectively. The amino acid sequences of human PGC-1, PGC-1α and PGC-1β are provided herein as SEQ ID NOs: 2, 4, and 6, respectively.

PGC-1 was initially identified as a PPARγ-interacting protein from a brown adipose tissue (BAT) library and was subsequently found to associate with an array of nuclear receptors (NRs) and transcription factors (Puigserver, P. et al. (1998) *Cell* 92:829-839; Wu, Z. et al. (1999) *Cell* 98:115-124; Vega, R. B. et al. (2000) *Mol. Cell. Biol.* 20:1868-1876; Michael, L. F. et al. (2001) *Proc. Natl. Acad. Sci. USA* 98:3820-3825). PGC-1 has been shown to coordinately regulate the program of mitochondrial biogenesis and adaptive thermogenesis in BAT and skeletal muscle, mainly through the coactivation of PPARs and nuclear respiratory factor 1 (NRF1), a nuclear transcription factor that regulates the expression of many mitochondrial genes (Puigserver et al. (1998) supra; Wu et al. (1999) supra). In transgenic mice, PGC-1 increases mitochondrial biogenesis and β-oxidation of fatty acids in the heart, likely through augmentation of PPARα and NRF1 transcriptional activity (Lehman, J. J. et al. (2000) *J. Clin. Invest.* 106:847-856). Recently, PGC-1 expression was found to be elevated in fasted liver and several models of type-1 and type-2 diabetes; in addition, PGC-1 can directly control the activation of hepatic gluconeogenesis (Yoon, J. C. et al. (2001) *Nature* 413:131-138; Herzig, S. et al. (2001) *Nature* 413:179-183).

Importantly, PGC-1 has been described as a coactivator of nuclear receptors and has been shown to play a major role in cellular respiration, adaptive thermogenesis, and gluconeogenesis in tissues such as brown fat and skeletal muscle (Puigserver, P. et al. (1998) *Cell* 92:829-839; Wu, Z. et al. (1999) *Cell* 98:115-124; Yoon J. C. et al. (2001) *Nature* 413(6852): 131-8. As set forth above, the fact that PGC-1 activates respiration combined with the discoveries of the instant invention, i.e., the discovery of a previously unknown feedback loop in which decreasing the output of respiration leads to an increase in PGC-1 levels, implicates PGC-1 as a major target for use in determining the safe dosage range of a respiration uncoupling agent for use as a therapeutic.

One aspect of the invention pertains to methods utilizing isolated nucleic acid molecules that encode PGC-1 or biologically active portions thereof, as well as nucleic acid fragments sufficient for use as hybridization probes to identify PGC-1-encoding nucleic acid (i.e., PGC-1 mRNA). As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PGC-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, i.e., a nucleic acid molecule having the nucleotide sequence of SEQ ID NOs:1, 3 or 5 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs:1, 3 or 5 or a portion thereof (i.e., 400, 450, 500, or more nucleotides), can be isolated using standard molecular biology techniques and the sequence information provided herein. For example, a human PGC-1 cDNA can be isolated from a human liver, heart, kidney, or brain cell line (from Stratagene, LaJolla, Calif., or Clontech, Palo Alto, Calif.) using all or portion of SEQ ID NOs:1, 3 or 5 as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of SEQ ID NOs:1, 3 or 5 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs:1, 3 or 5 can be isolated by the polymerase chain reaction using oligonucleotide primers designed based upon the sequence of SEQ ID NOs:1, 3 or 5 or the homologous nucleotide sequence. For example, mRNA can be isolated from liver cells, heart cells, kidney cells, brain cells, or brown adipocytes (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs:1, 3 or 5 or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PGC-1 nucleotide sequence can be prepared by standard synthetic techniques, i.e., using an automated DNA synthesizer.

Probes based on the PGC-1 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a PGC-1 protein, such as by measuring a level of a PGC-1-encoding nucleic acid in a sample of cells from a subject, i.e., detecting PGC-1 mRNA levels.

Moreover, nucleic acid molecules encoding other PGC-1 family members and thus which have a nucleotide sequence which differs from the PGC-1 sequences of SEQ ID NOs:1, 3 or 5 are intended to be of the invention. For example, the use of alternately-spliced isoforms of PGC-1, referred to herein as PGC-1b and PGC-1c, or a PGC-1 homologue referred to herein as PGC-1β may be used in the methods of the invention. The nucleotide and amino acid sequences of mouse PGC-1b are described in U.S. patent application Ser. No. 10/482,094, incorporated herein by reference. The nucleotide and amino acid sequences of mouse PGC-1c are also described in U.S. patent application Ser. No. 10/482,094. The nucleotide and amino acid sequences of human and mouse PGC-1β are described in U.S. patent application Ser. No. 10/290,544, and in Lin, J. et al. (2002) *J. Biol. Chem.* 277(3): 1645-8, incorporated herein by reference. The nucleotide and amino acid sequences of mouse PGC-1 are also described in GenBank Accession Nos. AF453324 and AAL47054, respectively.

Additionally, other PGC-1 family members, for example a PGC-3 cDNA, can be identified based on the nucleotide sequence of human PGC-1 or mouse PGC-1. (It should be noted that a gene called PPARγ coactivator 2, or PGC-2, has already been described in the literature (Castillo, G. et al. (1999) *EMBO J.* 18(13):3676-87). However, PGC-2 is both structurally and functionally unrelated to PGC-1. Moreover, nucleic acid molecules encoding PGC-1 proteins from different species, and thus which have a nucleotide sequence which differs from the PGC-1 sequences of SEQ ID NOs:1, 3 or 5 are intended to be within the scope of the invention. For example, rat or monkey PGC-1 cDNA can be identified based on the nucleotide sequence of a human PGC-1.

In addition to the nucleic acid molecules encoding PGC-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1 coding strand, or to only a portion thereof. In one embodiment, an antisense nucleic acid molecule is antisense to a "coding region" of the coding strand of a nucleotide sequence encoding PGC-1. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PGC-1. The term "noncoding region" refers to 5' and 3' sequences which flank the coding region that are not translated into amino acids (i.e., also referred to as 5' and 3' untranslated regions).

PGC-1 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, PGC-1 levels are ascertained by measuring gene transcript (e.g. mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the PGC-1 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding PGC-1. Other suitable probes for use in the diagnostic assays of the invention are described herein. Hybridization of an mRNA with the probe indicates that PGC-1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the PGC-1 mRNA expression levels.

An alternative method for determining the PGC-1 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the PGC-1 mRNA.

As an alternative to making determinations based on the absolute PGC-1 expression level, determinations may be based on the normalized PGC-1 expression level. Expression levels are normalized by correcting the absolute PGC-1 expression level by comparing its expression to the expression of a non-PGC-1 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a PGC-1 protein can also be detected and/or quantified by detecting or quantifying the expressed polypeptide. The PGC-1 polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express PGC-1.

In one embodiment, an isolated PGC-1 protein, or a portion or fragment thereof, can be used as an immunogen to generate antibodies that bind PGC-1 using standard techniques for polyclonal and monoclonal antibody preparation. The full-length PGC-1 protein can be used or, alternatively, antigenic peptide fragments of PGC-1 can be used as immunogens. A PGC-1 immunogen typically is used to prepare antibodies by immunizing a suitable subject, (e.g., rabbit, goat, mouse or other mammal) with the immunogen. An appropriate immunogenic preparation can contain, for example, recombinantly expressed PGC-1 protein or a chemically synthesized PGC-1 peptide. The preparation can further include an adjuvant, such as Freund's complete or incomplete adjuvant, or similar immunostimulatory agent. Immunization of a suitable subject with an immunogenic PGC-1 preparation induces a polyclonal anti-PGC-1 antibody response.

Accordingly, another aspect of the invention pertains to the use of anti-PGC-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PGC-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PGC-1. The term "monoclonal antibody" or "monoclonal antibody composition", as used herein, refers to a population of antibody molecules that contain only one species of an antigen binding site capable of immunoreacting with a particular epitope of PGC-1. A monoclonal antibody composition thus typically displays a single binding affinity for a particular PGC-1 protein with which it immunoreacts.

Polyclonal anti-PGC-1 antibodies can be prepared as described above by immunizing a suitable subject with a PGC-1 immunogen. The anti-PGC-1 antibody titer in the immunized subject can be monitored over time by standard techniques, such as with an enzyme linked immunosorbent assay (ELISA) using immobilized PGC-1. If desired, the antibody molecules directed against PGC-1 can be isolated from the mammal (e.g., from the blood) and further purified by well known techniques, such as protein A chromatography to obtain the IgG fraction. At an appropriate time after immunization, i.e., when the anti-PGC-1 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a PGC-1 immunogen as described above, and the culture supernatants of the resulting hybridoma cells are screened to identify a hybridoma producing a monoclonal antibody that binds PGC-1.

Any of the many well known protocols used for fusing lymphocytes and immortalized cell lines can be applied for the purpose of generating an anti-PGC-1 monoclonal antibody (see, i.e., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3—NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1, i.e., using a standard ELISA assay.

Alternative to preparing monoclonal antibody-secreting hybridomas, a monoclonal anti-PGC-1 antibody can be identified and isolated by screening a recombinant combinatorial immunoglobulin library (e.g., an antibody phage display library) with PGC-1 to thereby isolate immunoglobulin library members that bind PGC-1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223, 409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-PGC-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/

02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PGC-1 antibody (e.g., monoclonal antibody) can be used to isolate PGC-1 by standard techniques, such as affinity chromatography or immunoprecipitation. An anti-PGC-1 antibody can facilitate the purification of natural PGC-1 from cells and of recombinantly produced PGC-1 expressed in host cells. Moreover, an anti-PGC-1 antibody can be used to detect PGC-1 protein (e.g., in a cellular lysate or cell supernatant) in order to evaluate the abundance and pattern of expression of the PGC-1 protein. Anti-PGC-1 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In vivo techniques for detection of PGC-1 protein include introducing into a subject a labeled antibody directed against the protein. For example, the antibody can be labeled with a radioactive marker whose presence and location in a subject can be detected by standard imaging techniques.

I. Methods of the Invention

The methods of the invention relate to the identification and use of therapeutic and prophylactic compositions for treating obesity or obesity-related disorders or preventing obesity or obesity-related disorders, e.g., Type II diabetes, in a subject. The compositions of the present invention include an effective amount of a respiration uncoupling agent in a pharmaceutically acceptable carrier. Other aspects of the invention include packaged respiration uncoupling agent(s). The packaged compounds and agents may also include instructions for using the respiration uncoupling agent for treating obesity or obesity-related disorders or preventing obesity or obesity-related disorders cells.

In another aspect, the invention relates to methods for treating obesity or obesity-related disorders, e.g., Type II diabetes, in a subject by administering to a subject an effective amount of a respiration uncoupling agent. The methods of the present invention allow for the determination of a safe and effective dosage of the respiration uncoupling agent required to be effective, resulting in fewer side effects in the subject being treated.

In general, the methods of the invention include a step of administering to a subject a respiration uncoupling agent for promoting metabolic activity. As used herein, "metabolic activity" includes an activity exerted by an adipose cell, or an activity that takes place in an adipose cell. For example, such activities include cellular processes that contribute to the physiological role of adipose cells, such as lipogenesis and lipolysis and include, but are not limited to, cell proliferation, differentiation, growth, migration, programmed cell death, uncoupled mitochondrial respiration, and thermogenesis.

As used herein, the term "cell death" includes the processes by which mammalian cells die or become terminally differentiated. Such processes include apoptosis (both reversible and irreversible) and processes thought to involve apoptosis (e.g., cell senescence), as well as necrosis and terminal cell differentiation. Cell death is typically manifested by the exposure of the internal membrane phospholipid phosphatidylserine (PS) on the outer leaflet of the plasma membrane and can be detected by art recognized methods.

As used herein the term "apoptosis" includes programmed cell death which can also be detected using techniques which are known in the art. For example, apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay.

In another aspect, the invention features methods for inhibiting the proliferation of adipocytes by contacting the cells with a respiration uncoupling agent. In general, the method includes a step of contacting adipocytes with a respiration uncoupling agent effective for reducing the proliferation of adipocytes. The reduced proliferation of adipocytes can be detected by at least one of the following biological activities: (1) a decrease in the fraction of cells in the DNA synthesis phase of the cell cycle (S-phase); (2) an increase in expression of differentiation-associated markers; and (3) a decrease in the expression of proliferation-associated markers such as Ki-67 (MIB-1), e.g., a decrease in the expression of Ki-67 by about 30-50%, using techniques which are known in the art.

Changes in expression can occur in the protein or mRNA levels.

The present method can be performed on cells in culture, e.g., ex vivo, or can be performed on cells present in an animal subject, e.g., as part of an in vivo therapeutic protocol. The therapeutic regimen can be carried out on a human or other animal subject.

Particular examples of respiration uncoupling agents include, but are not limited to, DNP, FCCP and CCCP.

As used herein, the term "agent" and "therapeutic agent" is defined broadly as anything that cells from a subject with obesity or an obesity-related disorder may be exposed to in a therapeutic protocol. In the context of the present invention, such agents include, but are not limited to, respiration uncoupling agents, e.g., DNP, FCCP, and CCCP.

The term "administering" is intended to include routes of administration which allow the respiration uncoupling agent to perform its intended function of increasing metabolic activity. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the respiration uncoupling agent can be coated with or disposed in a selected material to protect it from natural conditions which may detrimentally effect its ability to perform its intended function. The respiration uncoupling agent can be administered alone, or in conjunction with a pharmaceutically acceptable carrier. Further the respiration uncoupling agent can be coadministered with a pharmaceutically acceptable carrier. The respiration uncoupling agent also can be administered as a prodrug which is converted to its active form in vivo.

Figure 9:
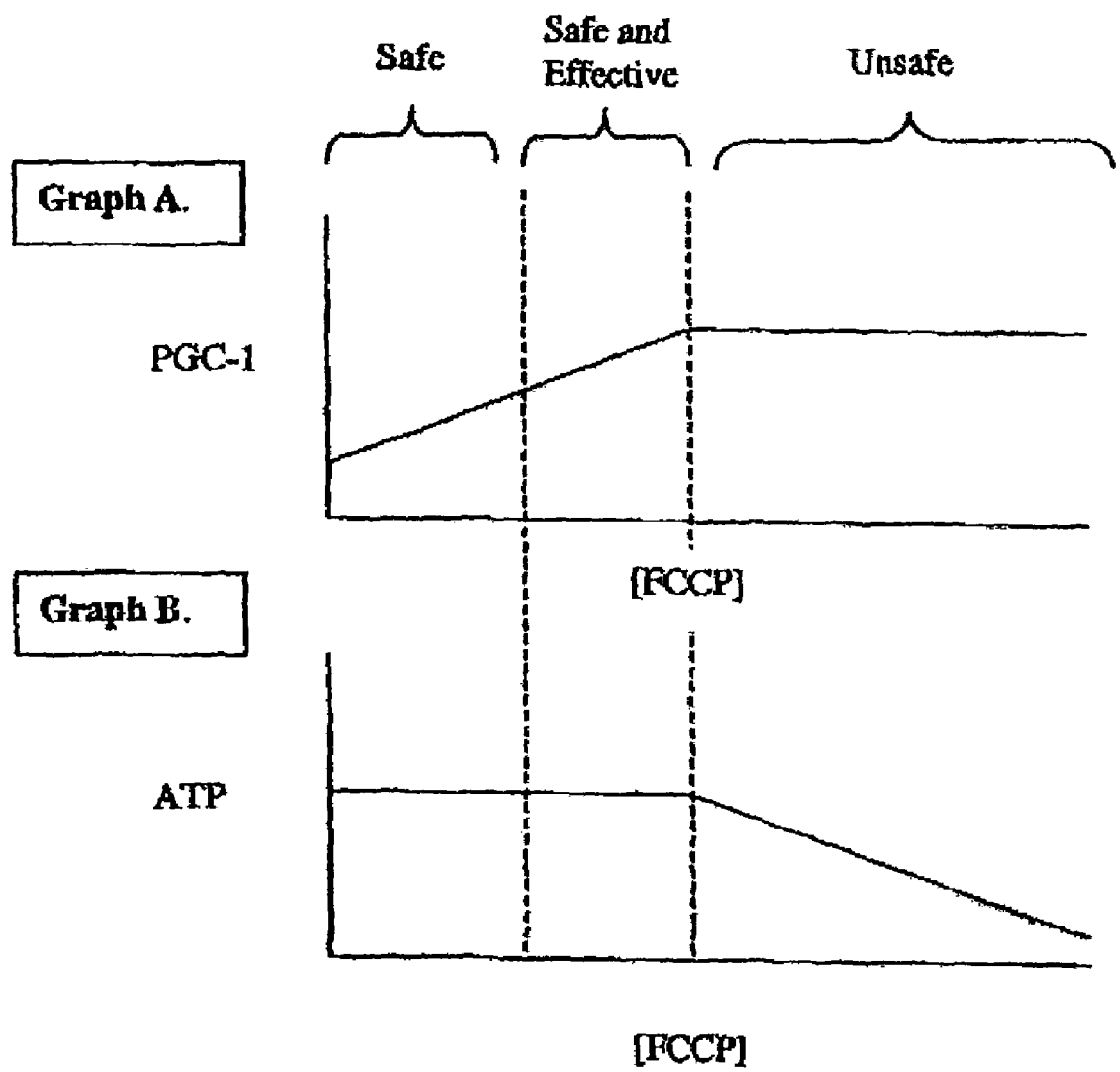
FIG. 9 depicts Graphs A and B, which illustrate an example of safe, safe and effective, and unsafe dosages of a respiration uncoupling agent, e.g., FCCP.

The language "effective amount" of the respiration uncoupling agent is that amount necessary or sufficient to promote metabolic activity in the subject or population of subjects. The effective amount can vary depending on such factors as the type of therapeutic agent(s) employed, the size of the subject, or the severity of the disorder. Determination of a therapeutically effective amount of a respiration uncoupling agent can be readily made as described herein (See FIG. 9, for example). Specifically, PGC-1 expression levels can be used to determine the "safe dosage range" of a known or putative respiration uncoupling agent. In particular, the time point at which PGC-1 levels stop increasing and remain substantially constant despite increasing levels of the respiration uncoupling agent, corresponds to the outer boundary of the safe dosage range of the respiration uncoupling agent. The "unsafe dosage range" of the respiration uncoupling agent corresponds to any time point during and after the maximum expression level of PGC-1 is achieved in the presence of the respiration uncoupling agent (see FIG. 9, for example).

In addition, a safe dosage range of a respiration uncoupling agent may also be determined by measuring modulation of metabolic rate, e.g., increased metabolic rate; modulation of oxygen consumption, e.g., increased oxygen consumption; modulation of cellular respiration, e.g., increased cellular respiration, ATP levels and/or body temperature.

Furthermore, because glycolysis is accelerated during uncoupling, lactic acidosis also acts as a marker for respiration uncoupling and may be monitored to identify a safe dosage range of a respiration uncoupling agent. Lactic acidosis is easily identified by measuring the level of lactate in the blood of a subject using methods known to one of skill in the art. In addition, because protein kinase is decreased when PGC-1 is effectively compensating for the decline in ATP levels caused by increased levels of respiration uncoupling agent, it may also be used as a marker for respiration uncoupling.

To determine the effective range (within a safe range), other considerations may be taken into account such as determining the level of uncoupling agent that is effective in causing weight loss in a subject or population of subjects. An effective dosage range of a respiration uncoupling agent may also be determined by analysis of one or more indicators of respiration uncoupling, or the effects thereof. For example, an effective dosage range may be determined by monitoring weight change, e.g., weight loss; change in fat mass, e.g., loss of fat mass; change in the level of adiposity; modulation of metabolic rate, e.g., increased metabolic rate; modulation of oxygen consumption, e.g., increased oxygen consumption; modulation of cellular respiration, e.g., increased cellular respiration.

Accordingly, in one embodiment, a safe dosage of a respiration uncoupling agent includes a dosage at which PGC-1 levels and metabolic rate are increased slightly, but body temperature and blood lactate levels are not increased. An effective dosage is a safe dosage which, in one embodiment, leads to a decrease in body weight and adiposity. Accordingly, PGC-1 and metabolic byproducts, e.g., lactic acid, can be used as markers to determine the safe and effective dosage of a respiration uncoupling agent.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances. U.S. Pat. No. 5,427,916, for example, describes a method for predicting the effectiveness of antineoplastic therapy in individual subjects, and illustrates certain methods which can be used in conjunction with the treatment protocols of the instant invention.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration uncoupling agent to treat obesity or obesity-related disorders can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

The invention also provides methods (also referred to herein as "screening assays") for identifying respiration uncoupling agents, i.e., candidate or test compounds or agents (e.g., peptides, peptidomimetics, small molecules or other drugs). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses PGC-1 is contacted with a test compound and the ability of the test compound to stimulate PGC-1 expression is determined. Determining the ability of the test compound to stimulate PGC-1 expression can be accomplished by, for example, antibody-based or PCR-based assays. The cell, for example, can be of mammalian origin, e.g., a liver cell, a skeletal muscle cell, or a fat cell, such as an adipocyte.

In an alternative embodiment, determining the ability of the test compound to stimulate PGC-1 expression can be accomplished by determining the ability of PGC-1 to further modulate the activity of a downstream effector of a PGC-1 target molecule.

In another embodiment, respiration uncoupling agents are identified in a method wherein a cell is contacted with a candidate compound and the expression of PGC-1, e.g., mRNA or polypeptide levels, in the cell is determined. The level of expression of PGC-1 mRNA or polypeptide levels in the presence of the candidate compound is compared to the level of expression of PGC-1 mRNA or polypeptide in the absence of the candidate compound, and/or compared to the level of expression of PGC-1 mRNA or polypeptide in the presence of a known respiration uncoupling agent. The candidate compound can then be identified as a modulator of PGC-1 expression based on this comparison. For example, when expression of PGC-1 mRNA or polypeptide is greater (statistically significantly greater) in the presence of the candidate compound than in its absence, the candidate compound is identified as a respiration uncoupling agent. Alternatively, when expression of PGC-1 mRNA or polypeptide is less (statistically significantly less) in the presence of the candidate compound than in its absence, the candidate compound is likely not a respiration uncoupling agent. Likewise, when expression of PGC-1 mRNA or polypeptide is substantially similar (i.e., not statistically different) to the expression in the presence of a known respiration uncoupling agent, the candidate compound is identified as a respiration uncoupling agent. The level of PGC-1 mRNA or polypeptide expression in the cells can be determined by methods described herein for detecting PGC-1 mRNA or polypeptide.

In another aspect, the invention pertains to a combination of two or more of the assays described herein. For example, a respiration uncoupling agent can be identified using a cell-based or a cell-free assay, and the ability of the agent to stimulate PGC-1 expression can be confirmed in vivo, e.g., in an animal such as an animal model for obesity or diabetes. Examples of animals that can be used include the transgenic mouse described in U.S. Pat. No. 5,932,779 that contains a mutation in an endogenous melanocortin-4-receptor (MC4-R) gene; animals having mutations which lead to syndromes that include obesity symptoms (described in, for example, Friedman, J. M. et al. (1991)*Mamm. Gen.* 1:130-144; Friedman, J. M. and Liebel, R. L. (1992) *Cell* 69:217-220; Bray, G. A. (1992) *Prog. Brain Res.* 93:333-341; and Bray, G. A. (1989) *Amer. J. Clin. Nutr.* 5:891-902); the animals described in Stubdal H. et al. (2000) *Mol. Cell. Biol.* 20(3):878-82 (the mouse tubby phenotype characterized by maturity-onset obesity); the animals described in Abadie J. M. et al. *Lipids* (2000) 35(6):613-20 (the obese Zucker rat (ZR), a genetic model of human youth-onset obesity and type 2 diabetes mellitus); the animals described in Shaughnessy S. et al. (2000) *Diabetes* 49(6):904-11 (mice null for the adipocyte fatty acid binding protein); the animals described in Loskutoff D. J. et al. (2000) *Ann. N.Y. Acad. Sci.* 902:272-81 (the fat mouse); or animals having mutations which lead to syndromes that include diabetes (described in, for example, Alleva et al. (2001) *J. Clin. Invest.* 107:173-180; Arakawa et al. (2001) *Br. J. Pharmacol.* 132:578-586; Nakamura et al. (2001) *Diabetes Res. Clin. Pract.* 51:9-20; O'Harte et al. (2001) *Regul. Pept.* 96:95-104; Yamanouchi et al. (2000) *Exp. Anim.* 49:259-266; Hoenig et al. (2000) *Am. J. Pathol.* 157: 2143-2150; Reed et al. (2000) *Metabolism* 49:1390-1394; and Clark et al. (2000) *J. Pharmacol. Toxicol. Methods* 43: 1-10). Other examples of animals that may be used include non-recombinant, non-genetic animal models of obesity such as, for example, rabbit, mouse, or rat models in which the animal has been exposed to either prolonged cold or long-term over-eating, thereby, inducing hypertrophy of BAT and increasing BAT thermogenesis (Himms-Hagen, J. (1990), supra).

This invention further pertains to novel agents identified by the above-described screening assays. Accordingly, it is within the scope of this invention to further use an agent identified as described herein in an appropriate animal model. For example, a respiration uncoupling agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Monitoring the influence of agents (e.g., drugs) on obesity and obesity-related disorders can be applied not only in basic drug screening, but also in clinical trials. In such clinical trials, the expression of PGC-1 can be used as a "read out." In addition, genes, including PGC-1, that are modulated in cells by treatment with the putative respiration uncoupling agent can be identified. Thus, to study the effect of respiration uncoupling agents on obesity and obesity-related disorders, for example, in a clinical trial, cells can be isolated and RNA prepared and analyzed for the levels of expression of PGC-1 and other genes implicated in the metabolism-associated disorder, respectively. The levels of gene expression (e.g., a gene expression pattern) can be quantified by northern blot analysis or RT-PCR, as described herein, or alternatively by measuring the amount of polypeptide produced, by one of the methods as described herein, or by measuring the levels of activity of PGC-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with a respiration uncoupling agent identified by the screening assays described herein, including the steps of (i) obtaining a pre-administration sample from a subject prior to administration of the agent; (ii) detecting the level of expression of a PGC-1 polypeptide, mRNA, or genomic DNA in the preadministration sample; (iii) obtaining one or more post-administration samples from the subject; (iv) detecting the level of expression of a PGC-1 polypeptide, mRNA, or genomic DNA in the post-administration samples; (v) comparing the level of expression or activity of the PGC-1 polypeptide, mRNA, or genomic DNA in the pre-administration sample with the PGC-1 polypeptide, mRNA, or genomic DNA in the post administration sample or samples; and (vi) altering the administration of the agent to the subject accordingly. For example, increased administration of the agent may be desirable to increase the expression or activity of PGC-1 to higher levels than detected, i.e., to increase the effectiveness of the agent. According to such an embodiment, PGC-1 expression may be used as an indicator of the boundaries of the safe dosage ranges and effectiveness of an agent, even in the absence of an observable phenotypic response.

The respiration uncoupling agents of the present invention identified by a screening assay described herein can be administered to individuals to treat (prophylactically or therapeutically) obesity and obesity-related disorders. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a respiration uncoupling agent as well as tailoring the dosage and/or therapeutic regimen of treatment with a respiration uncoupling agent, i.e., the methods of the present invention may be used to "custom fit" an appropriate dosage and treatment regime for a specific subject and/or subject population.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of subjects taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known, e.g., all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a respiration uncoupling agent of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, combined with the methods of the present invention, when applied to dosing or drug selection, can avoid adverse reactions or therapeutic failure and thus enhance therapeutic or prophylactic efficiency when treating a subject with a respiration uncoupling agent.

Kits

The invention also provides a kit for identifying the upper limit of a safe dosage range for a respiration uncoupling agent comprising a cell expressing PGC-1, an agent capable of determining the maximum PGC-1 expression levels, and instructions for use. The invention further provides a kit for identifying a compound capable of respiration uncoupling activity comprising a cell expressing PGC-1, an agent capable of determining the maximum PGC-1 expression level, and instructions for use. The agent capable of determining the maximum PGC-1 expression level is, for example, an anti-PGC-1 antibody, or an agent capable of detecting PGC-1 mRNA molecules. The kit may comprise a box or container that holds the components of the kit. The box or container is affixed with a label or a Food and Drug Administration approved protocol. The box or container holds components of the invention that are preferably contained within plastic, polyethylene, polypropylene, ethylene, or propylene vessels. The vessels can be capped-tubes or bottles.

The kit may, optionally, also include other compositions such as RNA and/or protein sampling means. RNA and or protein sampling means are well known to one of skill in the art and can include, but not be limited to substrates, such as filter papers, the AmpliCard.™. (University of Sheffield, Sheffield, England S10 2JF; Tarlow, J W, et al., *J. Invest. Dermatol.* 103:387-389 (1994)) and the like; RNA and/or protein purification reagents, lysis buffers, proteinase solutions and the like; RT- and PCR reagents, such as 10× reaction buffers, reverse transcriptase, thermostable polymerase, dNTPs, and the like; and Nylon membranes, transfer solutions, etc. PCR amplification oligonucleotides should hybridize between 25 and 2500 base pairs apart, preferably between about 100 and about 500 bases apart, in order to produce a PCR product of convenient size for subsequent analysis. The assay kit and method may also employ labeled oligonucleotides to allow ease of identification in the assays, e.g., RT-PCR, Northern blotting and/or Western blotting. Examples of labels which may be employed include radio-labels, enzymes, fluorescent compounds, streptavidin, avidin, biotin, magnetic moieties, metal binding moieties, antigen or antibody moieties, and the like.

II. Pharmaceutical Compositions

In another aspect, the present invention provides pharmaceutically acceptable compositions which comprise a therapeutically-effective amount of a respiration uncoupling agent formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of a respiration uncoupling agent, or composition comprising a respiration uncoupling agent which is effective for producing some desired therapeutic effect, e.g., weight loss, at a reasonable benefit/risk ratio.

The phrase "pharmaceutically acceptable" is employed herein to refer to those respiration uncoupling agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the respiration uncoupling agents encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the respiration uncoupling agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of respiration uncoupling agents. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a respiration uncoupling agent with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active respiration uncoupling agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a respiration uncoupling agent include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a respiration uncoupling agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The respiration uncoupling agent can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a respiration uncoupling agent in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier. Actual dosage levels of the active ingredients in the pharmaceutical compositions of this invention may be determined by the methods of the present invention so as to obtain an amount of the active ingredient which is effective to achieve the desired therapeutic response for a particular subject, composition, and mode of administration, without being toxic to the subject.

This invention is further illustrated by the following examples which should not be construed as limiting. The contents of all references, patent applications, patents, and published patent applications, as well as the Figures and the Sequence Listing, cited throughout this application are hereby incorporated by reference.

EXAMPLES

Example 1

FCCP Mediates Induction of PGC-1α Expression in Brown Fat

This example describes the expression of PGC-1α and PGC-1β RNA in HIB1B brown fat cells after treatments with FCCP or DNP. It also describes the downstream effects of FCCP treatment of HIB1B cells. Further, it describes the activation of AMP kinase after treatment with FCCP.

Materials and Methods

HIB1B Growth Conditions

HIB1B brown fat cells were grown in DMEM (10% cosmic calf serum)+0.25 mg/ml penicillin/streptomycin at 37° C., 10% $CO_2$.

Treatments and Procedures

In FIGS. 1A and 1B, HIB1B cells were treated with 25 μM FCCP for 0-25 hours. In FIG. 1C, HIB1B cells were treated for 5 hours with 0-200 μM FCCP. In FIG. 1D, cells were treated for 5 hours with either FCCP or DNP as indicated in the figure. RNA was extracted using trizol and was resuspended in $ddH_2O$. RNA was run on a 1% agarose-formaldehyde gel, and 30 ug of RNA was used per lane. The gel was transferred onto a nylon membrane, and the membrane was probed for the genes indicated in the figures. 36B4 was used as the loading control.

Figure 2:
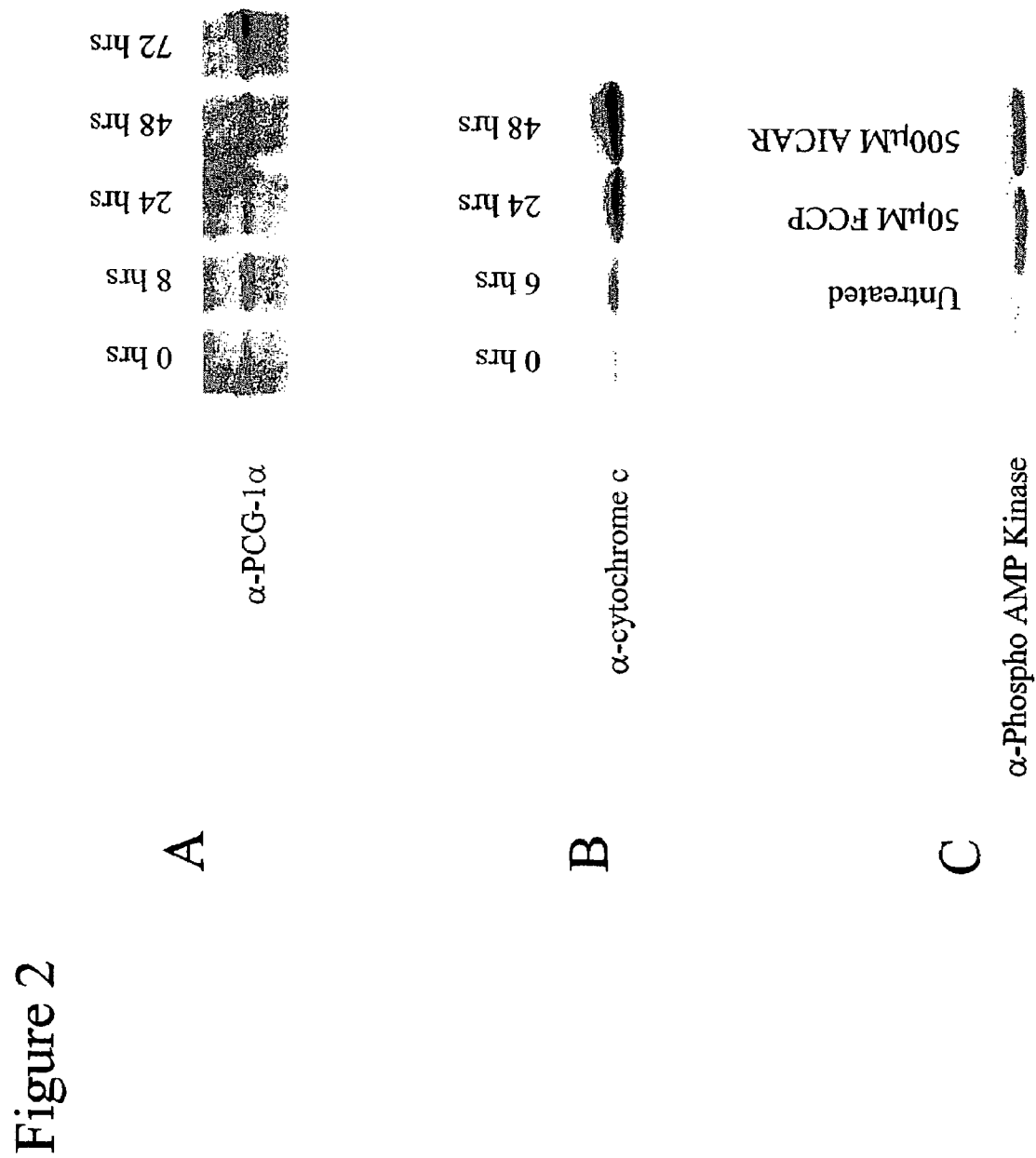
FIGS. 2A-2C are Western blots depicting the induction of PGC-1α protein expression in HIB1B brown fat cells due to long term mitochondrial stress caused by the uncoupling agent FCCP. (A) Cells were treated for up to 72 hours. PGC1α. protein levels increased with time after treatment with 2 μM FCCP. (B) HIB1B cells were treated for up to 48 hours with FCCP. The amount of cytochrome c protein was then measured and found to increase upon treatment with FCCP. (C) HIB1B cells were treated for 24 hours with either 50 μM FCCP or 500 μM AICAR, which is an activator of AMP Kinase and serves as the positive control. Phosphorylated (activated) AMPK was induced with FCCP treatment, and the induction was similar to that caused by AICAR.

In FIG. 2A, HIB1B cells were treated with 2 μM FCCP for 0-72 hours. In FIG. 2B, cells were treated with 50 μM FCCP for 0-48 hours. In FIG. 2C, cells were treated for 24 hours with either 50 μM FCCP or 500 μM AICAR, a compound that activates AMP Kinase. Protein was isolated, run on an SDS polyacrylamide gel, and transferred to a PVDF membrane, and blotted for the proteins indicated in the figures.

Figure 3:
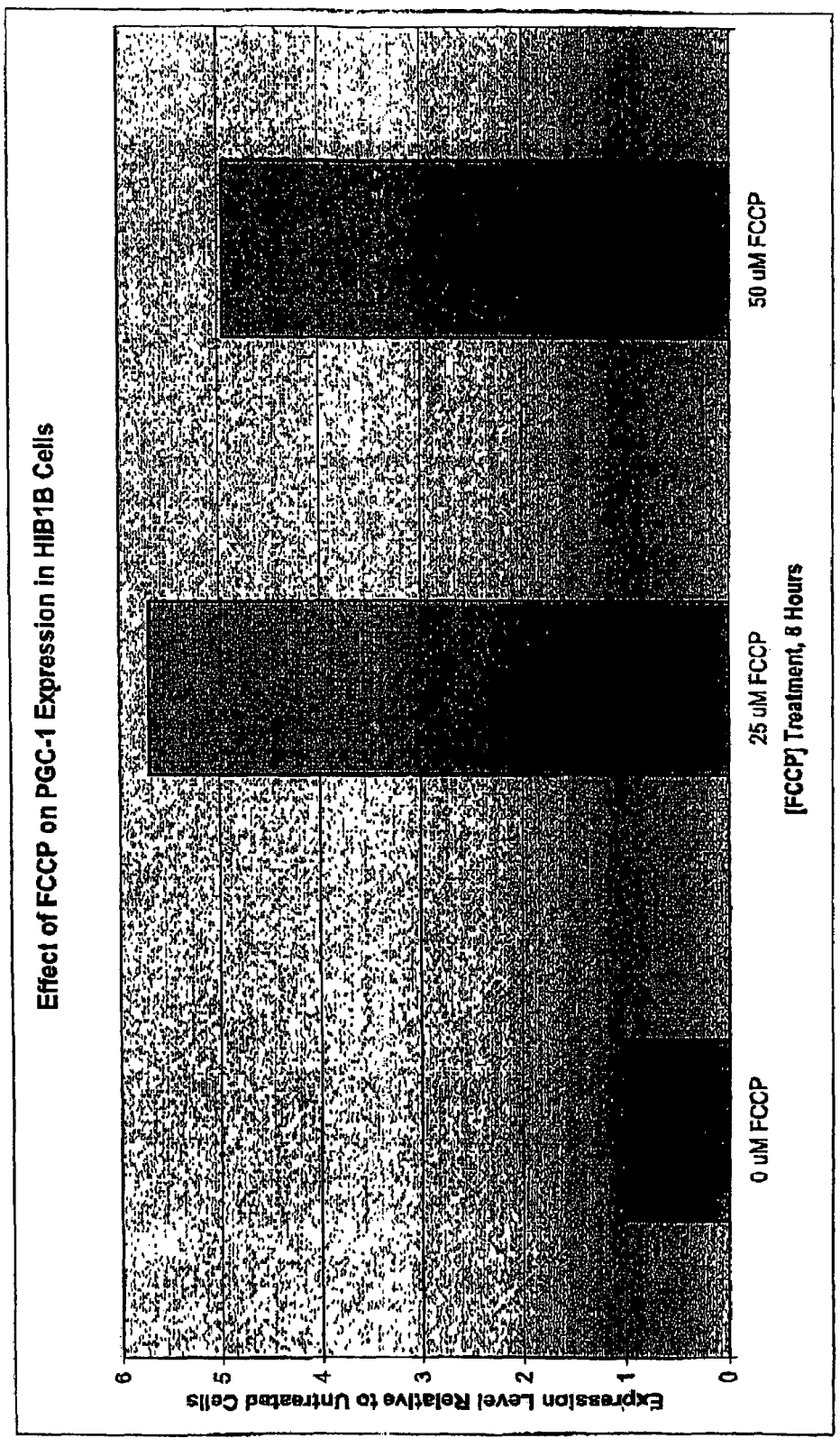
FIG. 3 is a graph demonstrating that high levels of FCCP do not cause further increases in PGC-1α expression level. HIB1B cells were treated with 25 μM FCCP and 50 μM FCCP for 8 hours. 25 μM FCCP caused a 5.5-fold induction of PGC-1 expression levels as measured by real time PCR. Treatment with 50 μM FCCP led to a 5-fold induction of PGC-1α levels. PGC-1α mRNA levels were normalized to TBP prior to analysis.

In FIG. 3, cells were treated for 8 hours as indicated on the figure. RNA was extracted as previously described and quantified using real time PCR. PGC-1α mRNA levels were normalized to TBP prior to analysis.

Results

Mitochondrial stress caused by the uncoupling agent FCCP induced PGC-1α and PGC-1β expression in HIB1B brown fat cells. FIG. 1A shows that PGC-1α expression levels were induced after 5 hours of treatment with 25 μM FCCP. The increased PGC-1α levels were sustained for 20 additional hours. As shown in FIG. 1B, PGC-1β expression levels were induced after 10-15 hours of treatment with 25 μM FCCP. PGC-1β levels remained induced until 25 hours of treatment. 36B4 expression levels served as a loading control. FIG. 1C shows that after 5 hours of treatment with increasing doses of FCCP, PGC-1α expression levels increased whereas PGC-1β expression levels did not increase. 36B4 is the loading control. As shown in FIG. 1D, like FCCP, dinitrophenol (DNP), another uncoupling agent, also caused an increase in PGC-1α expression after 5 hours of treatment. 36B4 is the loading control.

FIG. 2A shows that long term mitochondrial stress caused by the uncoupling agent FCCP induced PGC-1α protein expression. Similar treatment of HIB1B cells also induced cytochrome c protein levels as shown in FIG. 2B. Additionally, FIG. 2C shows that AMP Kinase was activated in cells treated for 24 hours with 50 μM FCCP similar to the activation induced by AICAR, a compound known to activate AMP Kinase. As shown in FIG. 2C, the amount of phospho-AMP kinase increased upon treatment with FCCP, indicating that uncoupling activates AMP kinase.

FIG. 3 illustrates the real time PCR quantification of PGC-1α expression in HIB1B cells treated with 25 μM and 50 μM FCCP for 8 hours. As was shown in the northern blot in FIG. 1A, FCCP treatment caused a 5-6 fold increase in PGC-1α expression.

Accordingly, respiration uncoupling agents, e.g., FCCP and DNP modulate, e.g., increase, expression of PGC-1α and PGC-1β in cells.

Example 2

FCCP Induction of Metabolic Stress

This example describes the cellular ATP levels in HIB1B brown fat cells after treatment with FCCP.

Materials and Methods

HIB1B Growth Conditions

HIB1B brown fat cells were grown in DMEM (10% cosmic calf serum)+0.25 mg/ml penicillin/streptomycin at 37° C., 10% $CO_2$.

Treatments and Procedures

Figure 4:
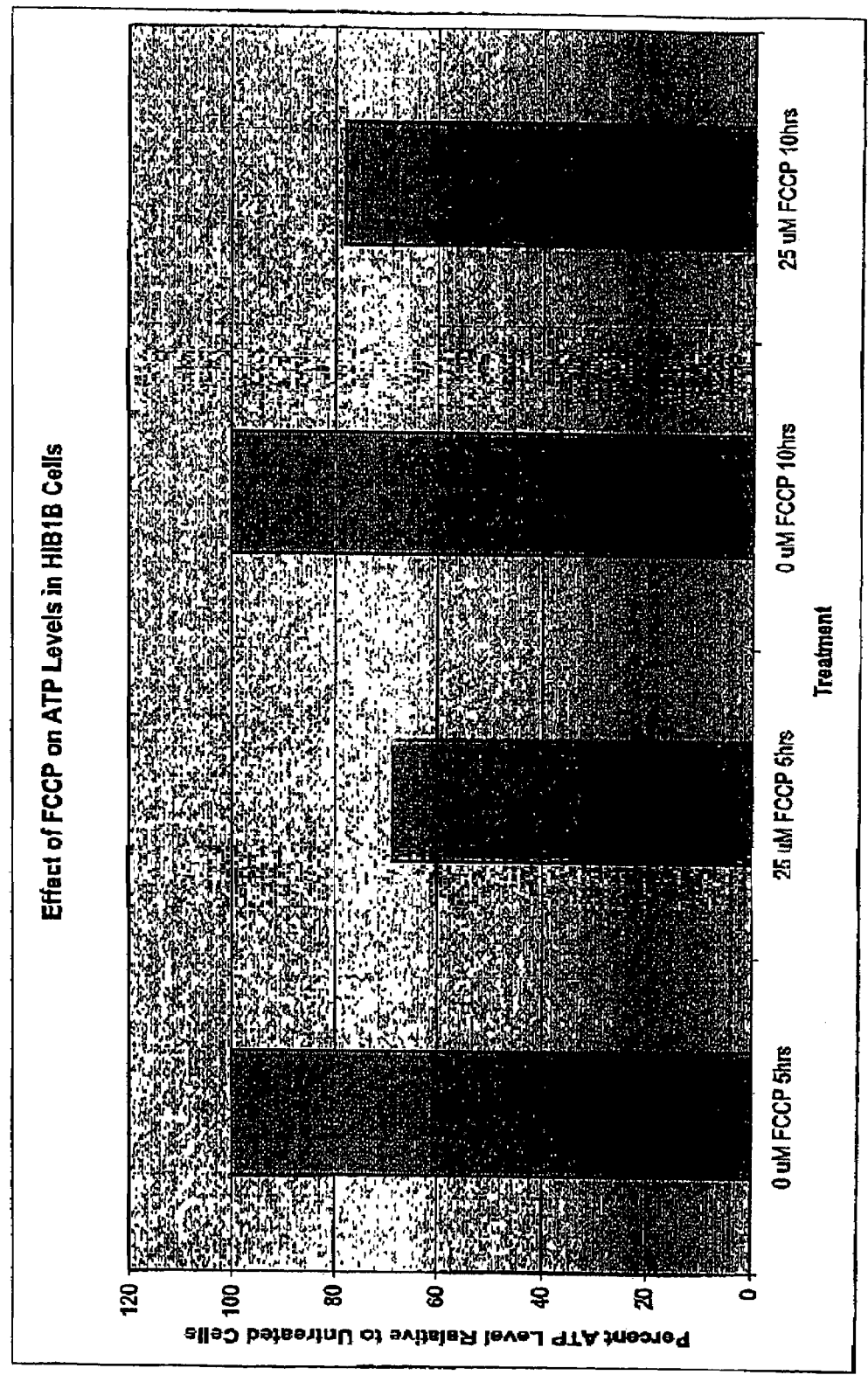
FIG. 4 is a graph demonstrating that treatment of HIB1B brown fat cells with 25 μM FCCP causes a decrease in cellular ATP levels. Cellular ATP levels dropped 25% in cells treated with FCCP for 5 hours. After 10 hours of treatment with FCCP, ATP levels were approximately 20% below that of untreated cells.

In FIG. 4, HIB1B cells were treated for either 5 or 10 hours with either 0 μM or 25 μM FCCP. ATP levels were measured using the Calbiochem ATP assay kit. For analysis, ATP levels were compared to those of untreated cells at the 5 and 10 hour time points.

Results

As shown in FIG. 4, treatment of HIB1B brown fat cells with 25 μM FCCP caused a decrease in cellular ATP levels. Cellular ATP levels dropped 25% in cells treated with FCCP for 5 hours. After 10 hours of treatment with FCCP, ATP levels were approximately 20% below that of untreated cells. Accordingly, respiration uncoupling agents act to reduce cellular ATP levels, and this reduction is sustained over at least 10 hours.

Example 3

Atractyloside/Antimycin A-Mediated Induction of PGC-1α

This example describes the expression of PGC-1α in HIB1B brown fat cells after treatment with Atractyloside, an inhibitor of the adenine nucleotide transporter, or Antimycin A, a complex III inhibitor.

Materials and Methods

HIB1B Growth Conditions

HIB1B brown fat cells were grown in DMEM (10% cosmic calf serum)+0.25 mg/ml penicillin/streptomycin at 37° C., 10% $CO_2$.

Treatments and Procedures

In FIG. 5A, HIB1B cells were treated with 0-15 μM Antimycin A, a Complex III inhibitor. In FIG. 5B, cells were treated for either 5 or 10 hours with 0-50 μM Atractlyoside, an adenine nucleotide transporter (ANT) inhibitor. RNA was extracted, run on a formaldehyde gel and transferred to a nylon membrane as previously described. Membranes were blotted for PGC-1α mRNA.

Results

As illustrated in FIG. 5, other mitochondrial inhibitors also caused PGC-1α expression levels to increase. FIG. 5A shows PGC-1α expression increased after treatment with 5 μM Antimycin A. In addition, FIG. 5B shows that PGC-1α expression increased after 5 hours of treatment with 50 μM atractyloside and 10 hours of treatment with 5 μM atractyloside.

Example 4

FCCP-Mediated Induction of PGC-1β in Liver Hepatoma Cells

This example describes the expression of PGC-1β and uncoupling protein 2 (UCP2) RNA (Fleury C. et al. (1998) *Nature Genetics* March; 15(3):269-72; Erlanson-Albertsson C (2003)*Acta Physiol Scand*. August; 178(4):405-12) in Fao liver hepatoma cells after treatment with FCCP.

Materials and Methods

Fao Growth Conditions

Fao liver hepatoma cells were grown in RPMI (10% fetal bovine serum)+0.25 mg/ml penicillin/streptomycin at 37° C., 5% $CO_2$.

Treatments and Procedures

In FIG. 6A, Fao liver hepatoma cells were treated with 2 μM FCCP for 0-48 hours. In FIGS. 6B and 6C, cells were treated for 24 hours with either 2 μM or 25 μM FCCP. RNA was extracted and analyzed as previously described. Membranes were blotted with either PGC-1β or UCP2 as indicated in the figure.

Results

As illustrated in FIG. 6, FCCP caused an increase in expression of PGC-1β and its target gene UCP2 in Fao liver hepatoma cells. FIG. 6A shows that PGC-1β expression levels increased after approximately 24 hours of treatment with 2 μM FCCP. FIGS. 6B and 6C show that both PGC-1β and UCP 2 expression levels increased after a 24 hour treatment with 2 μM and 25 μM FCCP.

Example 5

Calcium is Required for the FCCP-Mediated PGC-1α Induction

This example describes the role of calcium in the induction of PGC-1α, PGC-1β and mitochondrial genes.

Materials and Methods

Growth Conditions

HIB1B brown fat cells were grown in DMEM (10% cosmic calf serum)+0.25 mg/ml penicillin/streptomycin at 37° C., 10% $CO_2$. 10T 1/2 fibroblasts were grown in DMEM+ 10% fetal bovine serum+0.25 mg/ml penicillin/streptomycin at 37° C., 10% $CO_2$.

Treatments and Procedures

Figure 7:
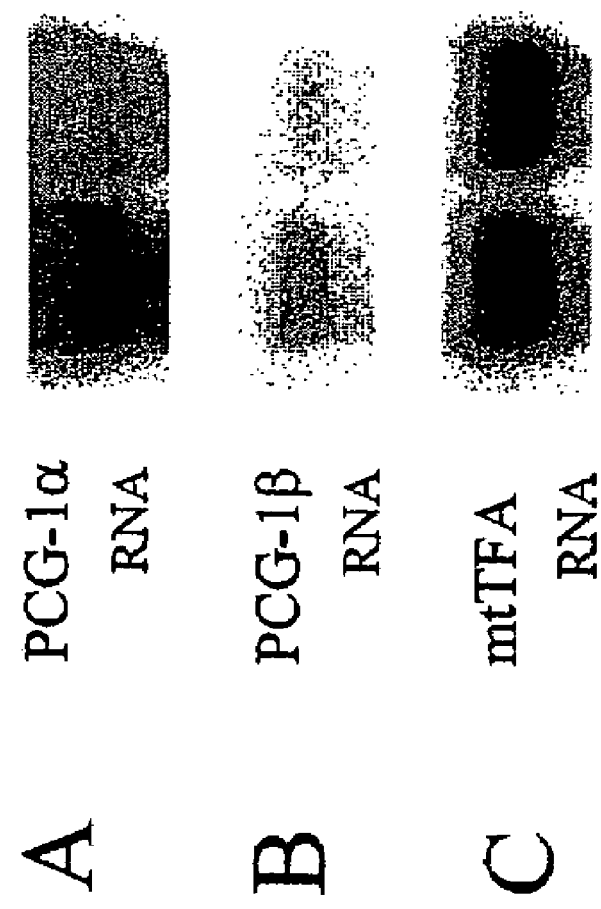
FIGS. 7A-7C are Northern blots demonstrating that PGC-1α is reduced in $p^0$ HIB1B cells which lack functional mitochondrial respiration (respiration is 95% reduced). (A) PGC-1α expression levels in $p^0$ HIB1B cells (B) PGC-1β expression levels in $p^0$ HIB1B cells. (C) mtTFA expression levels in $p^0$ HIB1B cells.
Figure 8:
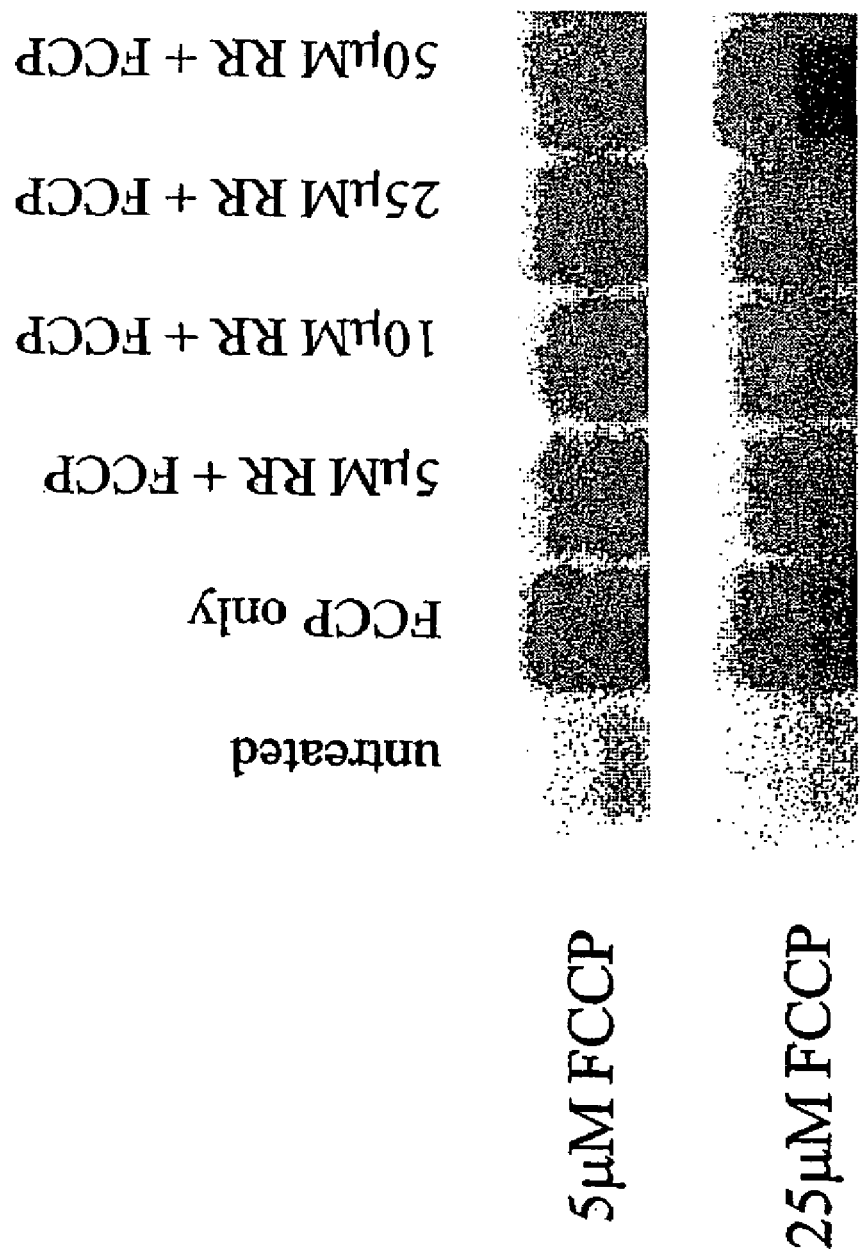
FIG. 8 depicts a Northern blot demonstrating that Ruthenium Red, an inhibitor of the mitochondrial $Ca^{2+}$ uniporter, blocks part of the FCCP-mediated induction of PGC-1α expression. HIB1B cells were treated for 5 hours with increasing concentrations of Ruthenium Red (RR) simultaneously with either 5 μM FCCP or 25 μM FCCP. FCCP-mediated PGC-1α expression was reduced after treatment with 5 μM RR, 10 μM RR, and 25 μM RR. This suggests that $Ca^{2+}$ released from the mitochondria upon treatment with FCCP plays a role in PGC-1 expression. 36B4 serves as the loading control.

In FIG. 7, HIB1B cells were treated for 5 hours with 0-50 μM Ruthenium Red (RR), an inhibitor of the mitochondrial $Ca^{2+}$ uniporter, simultaneously with either 5 μM or 25 μM FCCP as indicated in the figure. Untreated cells served as a control. RNA was extracted and analyzed as previously described. Membranes were blotted for PGC-1α. 36B4 served as the loading control.

10T 1/2 cells were treated with 50 μM FCCP, 10 μM BAPTA, a calcium chelator, or both FCCP and BAPTA for 16 hours. RNA was extracted using trizol and gene expression was measured using real time PCR. All expression levels were adjusted to actin and then the fold induction of expression was determined using the untreated cells as the control.

Results

Ruthenium Red (RR), an inhibitor of the mitochondrial $Ca^{2+}$ uniporter, blocked part of the FCCP-mediated induction of PGC-1α expression. As shown in FIG. 7, FCCP induced PGC-1α expression in HIB1B cells, which has been previously described. After treatment with both FCCP and RR, however, PGC-1α expression was reduced. This suggests that $Ca^{2+}$ released from the mitochondria upon treatment with FCCP plays a role in PGC-1 expression. 36B4 served as the loading control.

Figure 10:
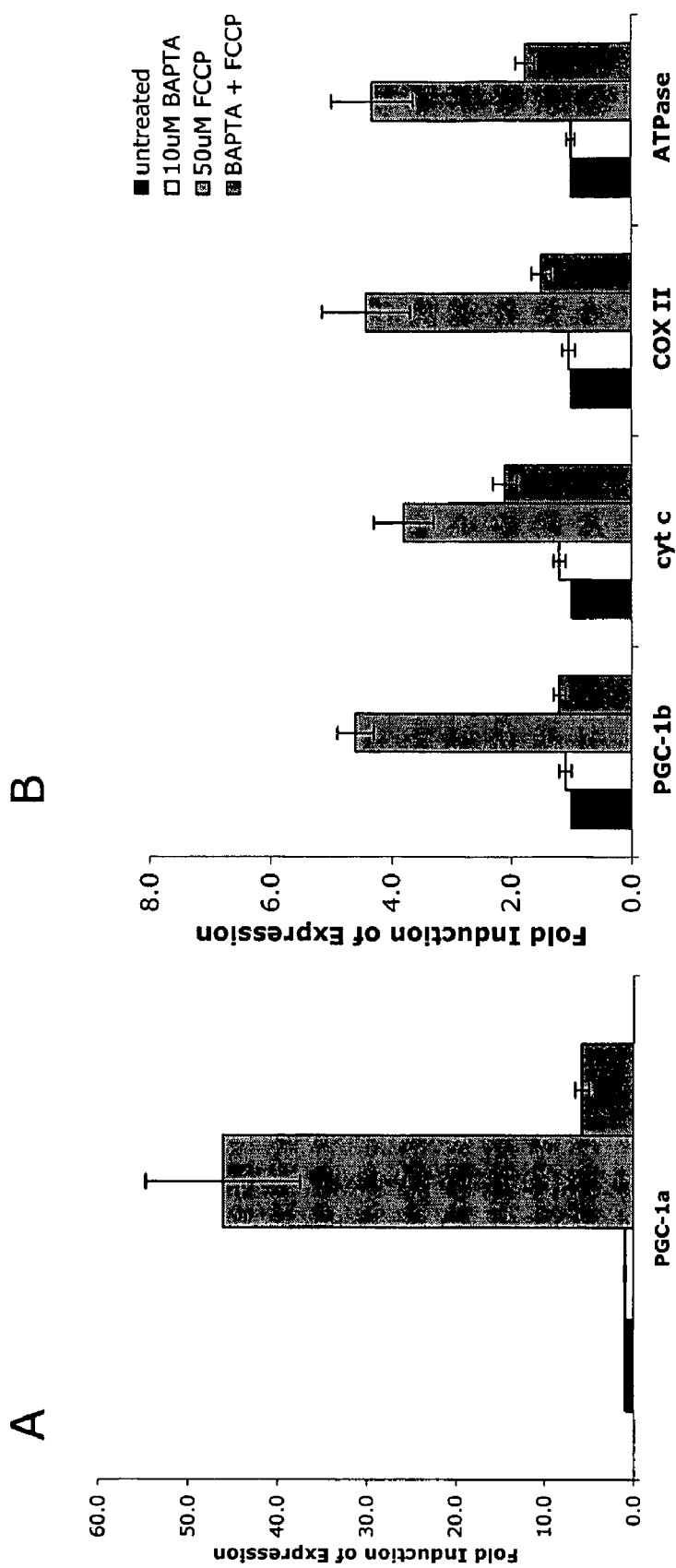
FIG. 10 show the induction of PGC-1α, PGC-1β and target genes requires calcium. (A) The FCCP-mediated induction of PGC-1α expression is blocked by treatment with BAPTA, a calcium chelator. 10T 1/2 fibroblasts were treated for 16 hours with 10 uM BAPTA, 50 uM FCCP or both BAPTA and FCCP. RNA was harvested and measured using real time PCR. (B) In the same experiment described in (A), the FCCP-mediated induction of PGC-1 β, cytochrome c, COX II and ATP synthase expression is blocked after treatment with BAPTA.

As shown in FIG. 10, the FCCP-mediated induction of PGC-1α, PGC-1β, cytochrome c, COX II and ATP synthase is blocked by co-treatment with BAPTA.

Example 6

Dose Response Curve for PGC-1α and Cell Viability

In this assay, the concentrations 1, 25, 50, 75, 100, 125, and 150 μM FCCP are used to treat HIB1B brown fat cells as previously described. After 10 and 24 hours of treatment, PGC-1α expression levels are measured using Northern blots and cell viability are measured using the trypan blue assay. This experiment determines the concentration of FCCP that will give maximal PGC-1α induction while maintaining cell viability.

In addition, in a second assay the concentrations 5, 25, 50 and 100 μM FCCP are used to treat 10T 1/2 fibroblasts. After 8 and 16 hours of treatment, PGC-1α expression levels are measured using real time PCR as described previously. Cell viability is measured using the trypan blue assay. This experiment determines the concentration of FCCP that will give maximal PGC-1α a induction while maintaining cell viability.

Example 7

Induction of PGC-1α in Muscle Cells

Muscle cells are treated as previously described for brown fat cells to induce PGC-1α expression levels. Alternatively, muscle cells are treated with FCCP as described in Example 11 for 10T 1/2 fibroblasts to induce PGC-1α expression. This experiment illustrates that FCCP has similar effects in cell types other than fat cells and fibroblasts.

Example 8

In Vivo Analysis of FCCP Treatment

This example describes the in vivo analysis of the effect of FCCP on PGC-1α expression levels in vivo in the treatment of mice. Mice are treated with a non-toxic concentration of FCCP; tissues such as brown fat, white fat, muscle and liver are extracted and PGC-1α expression levels are measured as previously described. This experiment illustrates the effect of FCCP on PGC-1α expression levels in vivo. It also determines the effect of FCCP on weight and fat composition, and illustrates the effectiveness of FCCP treatment in a physiological system.

Example 9

FCCP Treatment in PGC-1α Knockout Cells

PGC-1α knockout cells are treated with FCCP as previously described. This example shows whether the lack of PGC-1α has an effect of viability and whether PGC-1α is essential for the metabolic effects induced by FCCP.

Example 10

Increasing PGC-1α Expression In Vivo with FCCP to Promote Weight Loss

This example describes the effect of increasing PGC-1α (expression with the uncouplers FCCP and DNP in vivo in order to promote weight loss in an animal model.

As set forth herein, treatment of fibroblasts and preadipocytes in culture with FCCP and DNP causes an increase in PGC-1α. This experiment determines if FCCP or DNP cause an increase in PGC-1α in vivo, the lowest dose at which maximum PGC-1α levels can be achieved, and if PGC-1α can be used as a marker to determine the safe and effective concentration of FCCP of DNP necessary for weight loss.

FCCP (carbonylcyanide-p-trifluoromethoxyphenylhydrazone) is known as an uncoupling agent. DNP (2,4-dinitrophenol) is also known as an uncoupling agent. Uncouplers are chemicals that cause the mitochondria, the energy producing organelles in cells, to allow protons to more easily cross the inner membrane producing heat instead of producing ATP to be used for work inside the cell. This means that the mitochondria must utilize more substrate in order to maintain ATP levels in the cell. So, treatment of cells with uncoupling agents increases the metabolic rate of the cell.

Procedures:

The procedures to be used in these experiments are as follows: IP injections of the chemical uncoupling agent FCCP are performed daily (see experimental design for dose and time information). The body temperature of the mice is measured one hour after injections so as to monitor pain and distress. If the temperature rises above 42 degrees the mice are sacrificed. The following tissues are collected from euthanized mice: brown fat, skeletal muscle, and liver, which contribute the most to standard metabolic rate. In addition, heart, pancreas, large intestine, small intestine, gall bladder, spleen, brain, testes, and ovary are collected. Tissues are used to assess PGC-1 gene expression and protein levels.

Experimental Design:

Various studies from the 1930's using a different uncoupling agent called dinitrophenol used concentrations of about 5 mg/kg/day in rats. Since FCCP is more pure than DNP and the $LD_{50}$ for FCCP is approximately 5 times less than that of DNP, doses of FCCP are ⅕ the doses of DNP previously used. For example, a 50 g mouse is 0.05 kg, so it would have received 0.25 mg DNP/day according to the previous studies; this is equivalent to 0.05 mg FCCP/day. The maximum dose of FCCP that is used in this experiment is 0.5 mg/kg/day. The experiment is performed in C57 BL/6J and ob/ob (C57 BL/6J background) mice ordered from Jackson Laboratories.

Mice receive one IP injection of FCCP daily. The following experiment is repeated three times for statistical significance.

| Time | FCCP Dose/day |
|---|---|
| 1 day (24 hrs) | 25 ug, 50 ug, 100 ug, 250 ug, 500 ug |
| 2 days (48 hrs) | 25 ug, 50 ug, 100 ug, 250 ug, 500 ug |
| 1 week | 25 ug, 50 ug, 100 ug, 250 ug, 500 ug |
| 2 weeks | 25 ug, 50 ug, 100 ug, 250 ug, 500 ug |
| 1 month | 25 ug, 50 ug, 100 ug, 250 ug, 500 ug |

Body temperature is measured one hour after injections and weight is recorded every three days. Mice are sacrificed to avoid pain if the body temperature rises above 42 degrees. After the treatments as described above the mice are sacrificed using cervical dislocation with pre-anesthesia. Twenty-five mice are used in the first trial; depending on the results of the first trial, subsequent trials may require less than 25 mice as some experimental groups may not be necessary.

Results:

Treatment of mice with FCCP will cause an increase in PGC-1α RNA and protein levels in brown fat and muscle tissue, two of the three tissues that contribute the most to standard metabolic rate. A dose of FCCP is determined that will increase PGC-1α levels and metabolic rate slightly, but will not cause an increase in body temperature or blood lactate levels. This safe dose of FCCP leads to a decrease in body weight and adiposity, illustrating that PGC-1 and metabolic byproducts can be used as markers to determine the safe and effective dose of FCCP necessary to treat obesity.

Example 11

Uncoupling with FCCP and DNP Induces PGC-1α Expression

This examples describes the expression of PGC-1α and PGC-1β RNA in 10T 1/2 fibroblasts after treatment with FCCP. It also describes the increase in lactate concentration after treatment with FCCP.

Materials and Methods

Growth Conditions 10T 1/2 fibroblasts were grown in DMEM+10% fetal bovine serum+0.25 mg/ml penicillin/streptomycin at 37° C., 10% $CO_2$. HIB1B cells were grown in DMEM+10% cosmic calf serum+0.25 mg/ml penicillin/streptomycin at 37° C., 10% $CO_2$.

Treatments and Procedures

In FIG. 11A, 10T 1/2 cells were treated with 50 μM FCCP for 16 hours; in FIG. 11B, cells were treated for 72 hours with 25 μM FCCP. RNA was extracted using trizol and gene expression was measured using real time PCR. All expression levels were adjusted to actin and then the fold induction of expression was determined using the untreated cells as the control. In FIG. 11C, 10T 1/2 cells were treated for 16 hours with 50 μM FCCP. Lactate levels were measured using a lactate kit (Trinity Biotech), cells were counted, and lactate was graphed as mg lactate per million cells. In FIG. 12, HIB1B preadipocytes were treated with 25 μM FCCP, 250 μM DNP, 750 μM DNP or 1 mM DNP. RNA was extracted and run on a 1% agarose-formaldehyde gel (30 μg of RNA per lane). The gel was transferred to a nylon membrane and was probed for PGC-1α RNA and 36B4 RNA (36B4 represents the loading control).

Results

Figure 11:
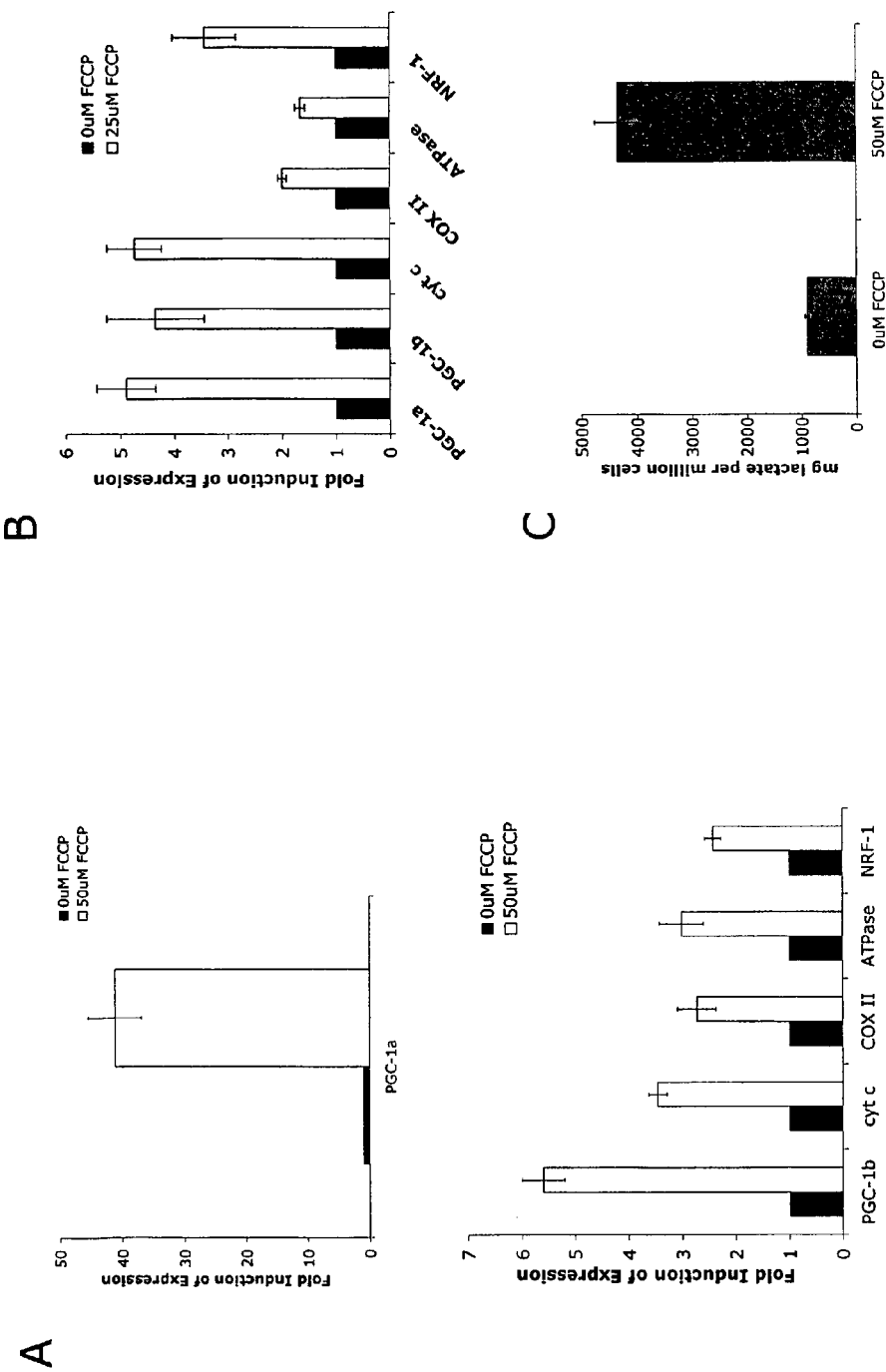
FIG. 11 shows that uncoupling induces the PGC-1 coactivators and their mitochondrial target genes. (A) FCCP treatment elevates the expression of PGC-1α, PGC-1β, cytochrome c, COX II, ATP synthase and NRF-1. 10T 1/2 fibroblasts were treated with or without 50 uM FCCP for 16 hours and RNA was measured using real time PCR. (B) The PGC-1 coactivators and their target genes remain elevated after long term treatment with FCCP. The experiment described in (A) was repeated but cells were treated for 72 hours with or without 25 uM FCCP. (C) Lactate levels increase with FCCP treatment. 10T 1/2 fibroblasts were treated with or without 50 uM FCCP for 16 hours and lactate concentrations were measured.
Figure 12:
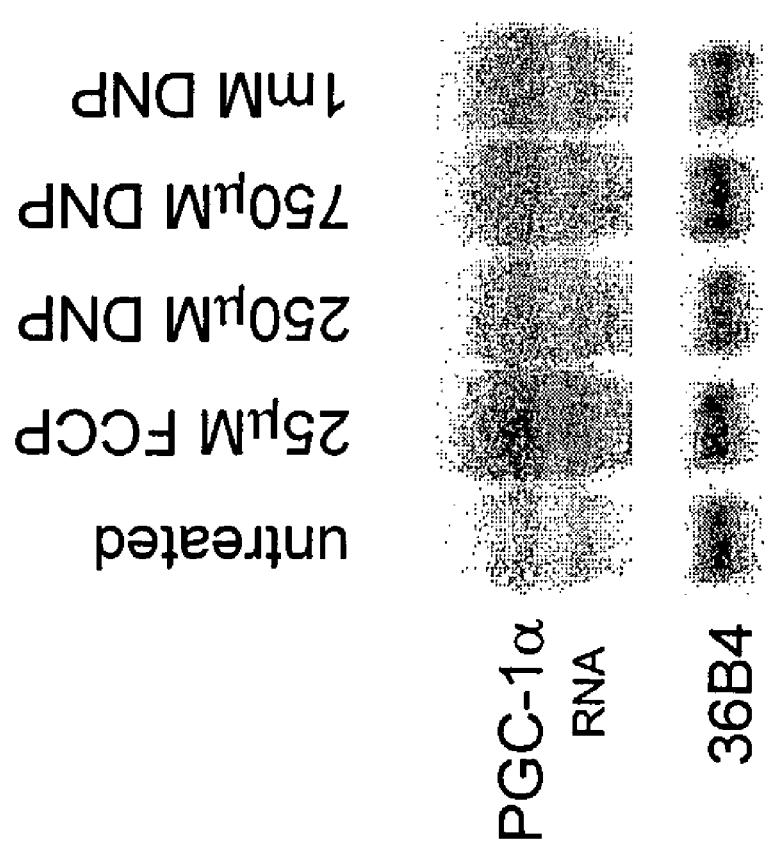
FIG. 12 show that uncoupling using 2,4-dinitrophenol (DNP) also increases PGC-1α expression. HIB1B preadipocytes were treated for 5 hours with three concentrations of DNP. FCCP treatment was used as a control. RNA was harvested and PGC-1α expression was measured with a northern blot. 36B4 represents the loading control.

As shown in FIG. 11, the uncoupler FCCP induced PGC-1α (and PGC-1β expression, cytochrome c, COX II, ATP synthase and NRF-1 expression, and lactate levels. Additionally, DNP induces PGC-1α expression (FIG. 12).

Example 12

The FCCP-Mediated Induction of PGC-1β and Mitochondrial Genes is Dependent on PGC-1α.

This example describes the dependence of PGC-1β and mitochondrial gene induction on PGC-1α.

Materials and Methods

Growth Conditions

Wild type and PGC-1α knock out preadipocytes were grown in DMEM+20% fetal bovine serum+0.25 mg/ml penicillin/streptomycin at 37° C., 10% $CO_2$.

Treatments and Procedures

Wild type and PGC-1α knock out preadipocytes were treated for 24 hours with or without 25 μM FCCP. RNA was extracted using trizol and gene expression was measured using real time PCR. All expression levels were adjusted to actin and then the fold induction of expression was determined using the untreated cells as the control.

Results

Figure 13:
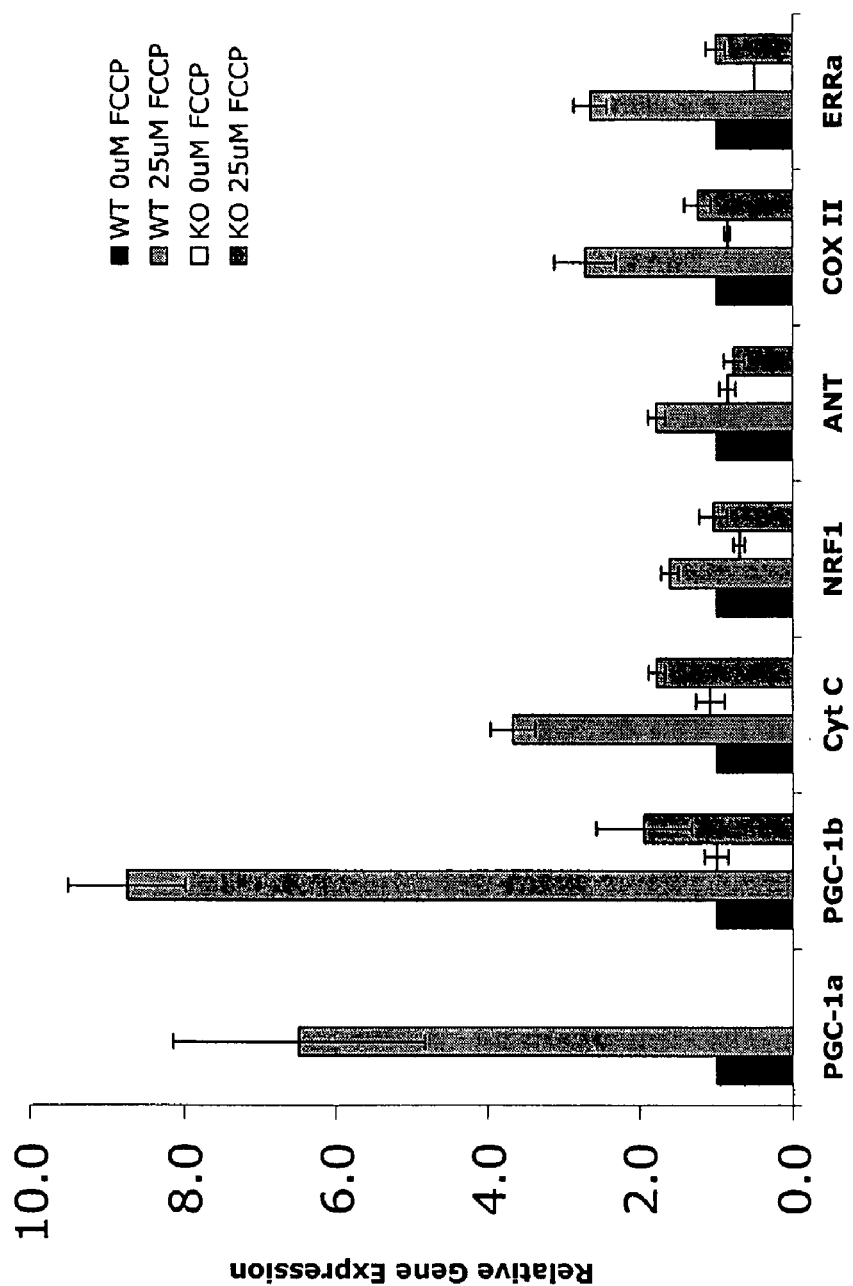
FIG. 13 show the induction of mitochondrial target genes and PGC-1β is dependent on PGC-1α. Wild type (WT) and PGC-1α knock out preadipocytes (KO) were treated with or without 25 uM FCCP for 24 hours. RNA was harvested and measured using real time PCR.

As shown in FIG. 13, in cells that lack PGC-1α, the induction of PGC-1β, cytochrome c, NRF-1, adenine nucleotide translocase (ANT), COX II and ERRα that normally occurs upon treatment with FCCP is blocked. This suggests that the induction of these genes depends on PGC-1α.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of identifying the upper limit of a safe dosage range for a respiration uncoupling agent comprising:
   a) contacting a cell expressing PGC-1 with varying amounts of the respiration uncoupling agent;
   b) determining the maximum PGC-1 expression level and the corresponding amount of the respiration uncoupling agent to thereby identify the upper limit of the safe dosage range for the respiration uncoupling agent.

2. The method of claim 1, wherein the respiration uncoupling agent is FCCP.

3. The method of claim 1, wherein the respiration uncoupling agent is selected from the group consisting of FCCP, DNP, and CCCP.

4. The method of claim 1, wherein the PGC-1 expression level is detected by an anti-PGC-1 antibody.

5. The method of claim 1, wherein the PGC-1 expression level is detected by the PGC-1 mRNA level.

6. The method of claim 1, wherein said method further comprises determining the level of ATP.

7. The method of claim 1, wherein said method further comprises determining the level of lactic acid.

8. The method of claim 1, wherein said method further comprises determining the metabolic rate of the cell.

9. The method of claim 1, wherein said method further comprises determining the level of AMP kinase.

10. The method of claim 1, further comprising determining whether said safe dosage is effective to increase metabolic activity by increasing the uncoupling of mitochondrial oxidative phosphorylation.

11. The method of claim 10, wherein said determining is carried out by identifying whether said safe dosage is capable of decreasing fat mass, decreasing adipocity, or increasing weight loss in a subject.

12. The method of claim 1, further comprising administering to the subject a safe dosage of a respiration uncoupling agent such that obesity or the obesity-related disorder is treated.

13. The method of claim 12, wherein the obesity related disorder is selected from the group consisting of obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia.

14. The method of claim 12, wherein the respiration uncoupling agent is FCCP.

15. The method of claim 12, wherein the respiration uncoupling agent is selected from the group consisting of FCCP, DNP, and CCCP.

16. The method of claim 12, wherein the PGC-1 expression level is detected by an anti-PGC-1 antibody.

17. The method of claim 12, wherein PGC-1 expression is detected by the PGC-1 mRNA level.

18. The method of claim 12, wherein the respiration uncoupling agent is administered intravenously.

19. The method of claim 12, wherein the respiration uncoupling agent is administered intraperitoneally.

20. The method of claim 12, wherein the respiration uncoupling agent is administered orally.

21. The method of claim 12, wherein said method further comprises determining the level of ATP.

22. The method of claim 12, wherein said method further comprises determining the level of lactic acid.

23. The method of claim 12, wherein said method further comprises determining the metabolic rate of the cell.

24. The method of claim 12, wherein said method further comprises determining the level of AMP kinase.

25. A method for increasing metabolic activity of a cell comprising contacting the cell with a safe dose of a respiration uncoupling agent, wherein the safe dose of the respiration uncoupling agent is identified by:
   a) contacting a cell expressing PGC-1 with varying amounts of the respiration uncoupling agent;
   b) determining the maximum PGC-1 expression level and the corresponding amount of the respiration uncoupling agent to thereby identify the upper limit of the safe dosage range for the respiration uncoupling agent.

26. The method of claim 25, wherein the respiration uncoupling agent is FCCP.

27. The method of claim 25, wherein the respiration uncoupling agent is selected from the group consisting of FCCP, DNP, and CCCP.

28. The method of claim 25, wherein the PGC-1 expression level is detected by an anti-PGC-1 antibody.

29. The method of claim 25, wherein the PGC-1 expression level is detected by determining the PGC-1 mRNA level.

30. The method of claim 25, wherein the cell is an adipocyte.

31. The method of claim 25, wherein the cell is selected from the group consisting of adipose cells, muscle cells and neural cells.

32. The method of claim 25, wherein said method further comprises determining the level of ATP.

33. The method of claim 25, wherein said method further comprises determining the level of lactic acid.

34. The method of claim 25, wherein said method further comprises determining the metabolic rate of the cell.

35. The method of claim 25, wherein said method further comprises determining the level of AMP kinase.

36. A method for identifying a compound capable of respiration uncoupling activity comprising:
   a) contacting a cell expressing PGC-1 with a test compound;
   b) assaying the ability of the test compound to stimulate the expression of PGC-1, thereby identifying a compound capable of respiration uncoupling activity; and
   c) identifying a safe dosage range of the respiration uncoupling agent.

37. The method of claim 36, wherein the safe dosage range of a respiration uncoupling agent is identified by:
   a) contacting a cell expressing PGC-1 with varying amounts of the respiration uncoupling agent;
   b) determining the maximum PGC-1 expression level and the corresponding amount of the respiration uncoupling agent to thereby identify the upper limit of the safe dosage range for the respiration uncoupling agent.

38. The method of claim 36, wherein said method further comprises determining the level of ATP.

39. The method of claim 36, wherein said method further comprises determining the level of lactic acid.

40. The method of claim 36, wherein said method further comprises determining the metabolic rate of the cell.

41. The method of claim 36, wherein said method further comprises determining the level of AMP kinase.

* * * * *

SEQUENCE LISTING

```
<160> NUMBER OF SEQ ID NOS: 6

<210> SEQ ID NO 1
<211> LENGTH: 3066
<212> TYPE: DNA
<213> ORGANISM: Homo sapiens
<220> FEATURE:
<221> NAME/KEY: CDS
<222> LOCATION: (92)...(2482)

<400> SEQUENCE: 1
aattcggcac gaggttgcct gcatgagtgt gtgctgtgtg tcagagtgga ttggagttga        60
aaaagcttga ctggcgtcat tcgggagctg g atg gct tgg gac atg tgc agc         112
                                   Met Ala Trp Asp Met Cys Ser
                                    1               5 caa gac tct gta tgg agt gac ata gag tgt gct gct ctg gtt ggt gag        160
Gln Asp Ser Val Trp Ser Asp Ile Glu Cys Ala Ala Leu Val Gly Glu
         10                  15                  20 gac cag cct ctt tgc cca gat ctt cct gaa ctt gac ctt tct gaa ctt        208
Asp Gln Pro Leu Cys Pro Asp Leu Pro Glu Leu Asp Leu Ser Glu Leu
     25                  30                  35 gat gtg aat gac ttg gat aca gac agc ttt ctg ggt gga ttg aag tgg        256
Asp Val Asn Asp Leu Asp Thr Asp Ser Phe Leu Gly Gly Leu Lys Trp
 40                  45                  50                  55 tgt agc gac caa tcg gaa atc ata tcc aac cag tac aac aat gag cct        304
Cys Ser Asp Gln Ser Glu Ile Ile Ser Asn Gln Tyr Asn Asn Glu Pro
                 60                  65                  70 gcg aac ata ttt gag aag ata gat gaa gag aat gag gca aac ttg cta        352
Ala Asn Ile Phe Glu Lys Ile Asp Glu Glu Asn Glu Ala Asn Leu Leu
             75                  80                  85 gcg gtc ctc aca gag aca ctg gac agt ctc ccc gtg gat gaa gac gga        400
Ala Val Leu Thr Glu Thr Leu Asp Ser Leu Pro Val Asp Glu Asp Gly
         90                  95                 100 ttg ccc tca ttt gat gca ctg aca gat gga gcc gtg acc act gac aac        448
Leu Pro Ser Phe Asp Ala Leu Thr Asp Gly Ala Val Thr Thr Asp Asn
    105                 110                 115 gag gcc agt cct tcc tcc atg cct gac ggc acc cct ccc cct cag gag        496
```

```
Glu Ala Ser Pro Ser Ser Met Pro Asp Gly Thr Pro Pro Gln Glu
120             125             130             135 gca gaa gag ccg tct cta ctt aag aag ctc tta ctg gca cca gcc aac        544
Ala Glu Glu Pro Ser Leu Leu Lys Lys Leu Leu Leu Ala Pro Ala Asn
            140             145             150 act cag ctc agc tac aat gaa tgc agc ggt ctt agc act cag aac cat        592
Thr Gln Leu Ser Tyr Asn Glu Cys Ser Gly Leu Ser Thr Gln Asn His
            155             160             165 gca gca aac cac acc cac agg atc aga aca aac cct gcc att gtt aag        640
Ala Ala Asn His Thr His Arg Ile Arg Thr Asn Pro Ala Ile Val Lys
            170             175             180 acc gag aat tca tgg agc aat aaa gcg aag agc att tgt caa cag caa        688
Thr Glu Asn Ser Trp Ser Asn Lys Ala Lys Ser Ile Cys Gln Gln Gln
185             190             195 aag cca caa aga cgt ccc tgc tca gag ctt ctc aag tat ctg acc aca        736
Lys Pro Gln Arg Arg Pro Cys Ser Glu Leu Leu Lys Tyr Leu Thr Thr
200             205             210             215 aac gat gac cct cct cac acc aaa ccc aca gaa aac agg aac agc agc        784
Asn Asp Asp Pro Pro His Thr Lys Pro Thr Glu Asn Arg Asn Ser Ser
                220             225             230 aga gac aaa tgt gct tcc aaa aag aag tcc cat aca caa ccg cag tcg        832
Arg Asp Lys Cys Ala Ser Lys Lys Lys Ser His Thr Gln Pro Gln Ser
            235             240             245 caa cat gct caa gcc aaa cca aca act tta tct ctt cct ctg acc cca        880
Gln His Ala Gln Ala Lys Pro Thr Thr Leu Ser Leu Pro Leu Thr Pro
            250             255             260 gag tca cca aat gac ccc aag ggt tcc cca ttt gag aac aag act att        928
Glu Ser Pro Asn Asp Pro Lys Gly Ser Pro Phe Glu Asn Lys Thr Ile
265             270             275 gag cga acc tta agt gtg gaa ctc tct gga act gca ggc cta act cct        976
Glu Arg Thr Leu Ser Val Glu Leu Ser Gly Thr Ala Gly Leu Thr Pro
280             285             290             295 ccc aca act cct cct cat aaa gcc aac caa gat aac cct ttc aag gct       1024
Pro Thr Thr Pro Pro His Lys Ala Asn Gln Asp Asn Pro Phe Lys Ala
                300             305             310 tcg cca aag ctg aag ccc tct tgc aag acc gtg gtg cca ccg cca acc       1072
Ser Pro Lys Leu Lys Pro Ser Cys Lys Thr Val Val Pro Pro Pro Thr
            315             320             325 aag agg gcc cgg tac agt gag tgt tct ggt acc caa ggc agc cac tcc       1120
Lys Arg Ala Arg Tyr Ser Glu Cys Ser Gly Thr Gln Gly Ser His Ser
            330             335             340 acc aag aaa ggg ccc gag caa tct gag ttg tac gca caa ctc agc aag       1168
Thr Lys Lys Gly Pro Glu Gln Ser Glu Leu Tyr Ala Gln Leu Ser Lys
345             350             355 tcc tca ggg ctc agc cga gga cac gag gaa agg aag act aaa cgg ccc       1216
Ser Ser Gly Leu Ser Arg Gly His Glu Glu Arg Lys Thr Lys Arg Pro
360             365             370             375 agt ctc cgg ctg ttt ggt gac cat gac tac tgt cag tca ctc aat tcc       1264
Ser Leu Arg Leu Phe Gly Asp His Asp Tyr Cys Gln Ser Leu Asn Ser
            380             385             390 aaa acg gat ata ctc att aac ata tca cag gag ctc caa gac tct aga       1312
Lys Thr Asp Ile Leu Ile Asn Ile Ser Gln Glu Leu Gln Asp Ser Arg
            395             400             405 caa cta gac ttc aaa gat gcc tcc tgt gac tgg cag ggg cac atc tgt       1360
Gln Leu Asp Phe Lys Asp Ala Ser Cys Asp Trp Gln Gly His Ile Cys
            410             415             420 tct tcc aca gat tca ggc cag tgc tac ctg aga gag act ttg gag gcc       1408
Ser Ser Thr Asp Ser Gly Gln Cys Tyr Leu Arg Glu Thr Leu Glu Ala
425             430             435
```

```
agc aag cag gtc tct cct tgc agc acc aga aaa cag ctc caa gac cag    1456
Ser Lys Gln Val Ser Pro Cys Ser Thr Arg Lys Gln Leu Gln Asp Gln
440             445                 450                 455 gaa atc cga gcg gag ctg aac aag cac ttc ggt cat ccc tgt caa gct    1504
Glu Ile Arg Ala Glu Leu Asn Lys His Phe Gly His Pro Cys Gln Ala
                460                 465                 470 gtg ttt gac gac aaa tca gac aag acc agt gaa cta agg gat ggc gac    1552
Val Phe Asp Asp Lys Ser Asp Lys Thr Ser Glu Leu Arg Asp Gly Asp
            475                 480                 485 ttc agt aat gaa caa ttc tcc aaa cta cct gtg ttt ata aat tca gga    1600
Phe Ser Asn Glu Gln Phe Ser Lys Leu Pro Val Phe Ile Asn Ser Gly
        490                 495                 500 cta gcc atg gat ggc cta ttt gat gac agt gaa gat gaa agt gat aaa    1648
Leu Ala Met Asp Gly Leu Phe Asp Asp Ser Glu Asp Glu Ser Asp Lys
505                 510                 515 ctg agc tac cct tgg gat ggc acg cag ccc tat tca ttg ttc gat gtg    1696
Leu Ser Tyr Pro Trp Asp Gly Thr Gln Pro Tyr Ser Leu Phe Asp Val
520                 525                 530                 535 tcg cct tct tgc tct tcc ttt aac tct ccg tgt cga gac tca gtg tca    1744
Ser Pro Ser Cys Ser Ser Phe Asn Ser Pro Cys Arg Asp Ser Val Ser
                540                 545                 550 cca ccg aaa tcc tta ttt tct caa aga ccc caa agg atg cgc tct cgt    1792
Pro Pro Lys Ser Leu Phe Ser Gln Arg Pro Gln Arg Met Arg Ser Arg
            555                 560                 565 tca aga tcc ttt tct cga cac agg tcg tgt tcc cga tca cca tat tcc    1840
Ser Arg Ser Phe Ser Arg His Arg Ser Cys Ser Arg Ser Pro Tyr Ser
        570                 575                 580 agg tca aga tca agg tcc cca ggc agt aga tcc tct tca aga tcc tgt    1888
Arg Ser Arg Ser Arg Ser Pro Gly Ser Arg Ser Ser Ser Arg Ser Cys
585                 590                 595 tac tac tat gaa tca agc cac tac aga cac cgc aca cac cgc aat tct    1936
Tyr Tyr Tyr Glu Ser Ser His Tyr Arg His Arg Thr His Arg Asn Ser
600                 605                 610                 615 ccc ttg tat gtg aga tca cgt tca agg tca ccc tac agc cgt agg ccc    1984
Pro Leu Tyr Val Arg Ser Arg Ser Arg Ser Pro Tyr Ser Arg Arg Pro
                620                 625                 630 agg tac gac agc tat gaa gcc tat gag cac gaa agg ctc aag agg gat    2032
Arg Tyr Asp Ser Tyr Glu Ala Tyr Glu His Glu Arg Leu Lys Arg Asp
            635                 640                 645 gaa tac cgc aaa gag cac gag aag cgg gag tct gaa agg gcc aaa cag    2080
Glu Tyr Arg Lys Glu His Glu Lys Arg Glu Ser Glu Arg Ala Lys Gln
        650                 655                 660 aga gag agg cag aag cag aaa gca att gaa gag cgc cgt gtg att tac    2128
Arg Glu Arg Gln Lys Gln Lys Ala Ile Glu Glu Arg Arg Val Ile Tyr
665                 670                 675 gtt ggt aaa atc aga cct gac aca acg cgg aca gaa ttg aga gac cgc    2176
Val Gly Lys Ile Arg Pro Asp Thr Thr Arg Thr Glu Leu Arg Asp Arg
680                 685                 690                 695 ttt gaa gtt ttt ggt gaa att gag gaa tgc acc gta aat ctg cgg gat    2224
Phe Glu Val Phe Gly Glu Ile Glu Glu Cys Thr Val Asn Leu Arg Asp
                700                 705                 710 gat gga gac agc tat ggt ttc atc acc tac cgt tac acc tgt gac gct    2272
Asp Gly Asp Ser Tyr Gly Phe Ile Thr Tyr Arg Tyr Thr Cys Asp Ala
            715                 720                 725 ttc gct gct ctt gag aat gga tat act tta cgc agg tcg aac gaa act    2320
Phe Ala Ala Leu Glu Asn Gly Tyr Thr Leu Arg Arg Ser Asn Glu Thr
        730                 735                 740 gac ttc gag ctg tac ttt tgt gga cgg aag caa ttt ttc aag tct aac    2368
Asp Phe Glu Leu Tyr Phe Cys Gly Arg Lys Gln Phe Phe Lys Ser Asn
745                 750                 755
```

```
tat gca gac cta gat acc aac tca gac gat ttt gac cct gct tcc acc    2416
Tyr Ala Asp Leu Asp Thr Asn Ser Asp Asp Phe Asp Pro Ala Ser Thr
760                 765                 770                 775 aag agc aag tat gac tct ctg gat ttt gat agt tta ctg aag gaa gct    2464
Lys Ser Lys Tyr Asp Ser Leu Asp Phe Asp Ser Leu Leu Lys Glu Ala
                780                 785                 790 cag aga agc ttg cgc agg taacgtgttc ccaggctgag gaatgacaga            2512
Gln Arg Ser Leu Arg Arg
            795 gagatggtca atacctcatg ggacagcgtg tcctttccca agactcttgc aagtcatact   2572 taggaatttc tcctacttta cactctctgt acaaaaataa aacaaaacaa aacaacaata   2632 acaacaacaa caacaacaat aacaacaaca accataccag aacaagaaca acggtttaca   2692 tgaacacagc tgctgaagag gcaagagaca gaatgataat ccagtaagca cacgtttatt   2752 cacgggtgtc agctttgctt tccctggagg ctcttggtga cagtgtgtgt gcgtgtgtgt   2812 gtgtgggtgt gcgtgtgtgt atgtgtgtgt gtgtacttgt ttggaaagta catatgtaca   2872 catgtgagga cttgggggca cctgaacaga acgaacaagg gcgacccctt caaatggcag   2932 catttccatg aagacacact taaaacctac aacttcaaaa tgttcgtatt ctatacaaaa   2992 ggaaaataaa taaatataaa aaaaaaaaaa aaaaactcg agagatctat gaatcgtaga    3052 tactgaaaaa cccc                                                    3066
```

<210> SEQ ID NO 2
<211> LENGTH: 6317
<212> TYPE: DNA
<213> ORGANISM: Homo sapiens

<400> SEQUENCE: 2

```
tagtaagaca ggtgccttca gttcactctc agtaaggggc tggttgcctg catgagtgtg     60
tgctctgtgt cactgtggat tggagttgaa aaagcttgac tggcgtcatt caggagctgg    120
atggcgtggg acatgtgcaa ccaggactct gagtctgtat ggagtgacat cgagtgtgct    180
gctctggttg gtgaagacca gcctctttgc ccagatcttc ctgaacttga tctttctgaa    240
ctagatgtga acgacttgga tacagacagc tttctgggtg gactcaagtg gtgcagtgac    300
caatcagaaa taatatccaa tcagtacaac aatgagcctt caaacatatt tgagaagata    360
gatgaagaga atgaggcaaa cttgctagca gtcctcacag agacactaga cagtctccct    420
gtggatgaag acggattgcc ctcatttgat gcgctgacag atggagacgt gaccactgac    480
aatgaggcta gtccttcctc catgcctgac ggcacccctc caccccagga ggcagaagag    540
ccgtctctac ttaagaagct cttactggca ccagccaaca ctcagctaag ttataatgaa    600
tgcagtggtc tcagtaccca gaaccatgca aatcacaatc acaggatcag aacaaaccct    660
gcaattgtta agactgagaa ttcatggagc aataaagcga agagtatttg tcaacagcaa    720
aagccacaaa gacgtccctg ctcggagctt ctcaaatatc tgaccacaaa cgatgaccct    780
cctcacacca aacccacaga gaacagaaac agcagcagag acaaatgcac ctccaaaaag    840
aagtcccaca cacagtcgca gtcacaacac ttacaagcca aaccaacaac tttatctctt    900
cctctgaccc cagagtcacc aaaatgaccc aagggttccc catttgagaa caagactatt    960
gaacgcacct taagtgtgga actctctgga actgcaggcc taactccacc caccactcct   1020
cctcataaag ccaaccaaga taacccttttt agggcttctc caaagctgaa gtcctcttgc   1080
aagactgtgg tgccaccacc atcaaagaag cccaggtaca gtgagtcttc tggtacacaa   1140
```

```
ggcaataact ccaccaagaa agggccggag caatccgagt tgtatgcaca actcagcaag    1200
tcctcagtcc tcactggtgg acacgaggaa aggaagacca agcggcccag tctgcggctg    1260
tttggtgacc atgactattg ccagtcaatt aattccaaaa cagaaatact cattaatata    1320
tcacaggagc tccaagactc tagacaacta gaaaataaag atgtctcctc tgattggcag    1380
gggcagattt gttcttccac agattcagac cagtgctacc tgagagagac tttggaggca    1440
agcaagcagg tctctccttg cagcacaaga aaacagctcc aagaccagga aatccgagcc    1500
gagctgaaca agcacttcgg tcatcccagt caagctgttt ttgacgacga agcagacaag    1560
accggtgaac tgagggacag tgatttcagt aatgaacaat tctccaaact acctatgttt    1620
ataaattcag gactagccat ggatggcctg tttgatgaca gcgaagatga aagtgataaa    1680
ctgagctacc cttgggatgg cacgcaatcc tattcattgt tcaatgtgtc tccttccttgt    1740 tcttctttta actctccatg tagagattct gtgtcaccac ccaaatcctt attttctcaa    1800 agacccaaa ggatgcgctc tcgttcaagg tccttttctc gacacaggtc gtgttcccga    1860
tcaccatatt ccaggtcaag atcaaggtct ccaggcagta gatcctcttc aagatcctgc    1920
tattactatg agtcaagcca ctacagacac cgcacgcacc gaaattctcc cttgtatgtg    1980
agatcacgtt caagatcgcc ctacagccgt cggcccaggt atgacagcta cgaggaatat    2040
cagcacgaga ggctgaagag ggaagaatat cgcagagagt atgagaagcg agagtctgag    2100
agggccaagc aaagggagag gcagaggcag aaggcaattg aagagcgccg tgtgatttat    2160
gtcggtaaaa tcagacctga cacaacacgg acagaactga gggaccgttt tgaagttttt    2220
ggtgaaattg aggagtgcac agtaaatctg cgggatgatg gagacagcta tggtttcatt    2280
acctaccgtt ataccgtgtga tgcttttgct gctcttgaaa atggatacac tttgcgcagg    2340
tcaaacgaaa ctgactttga gctgtacttt tgtggacgca agcaattttt caagtctaac    2400
tatgcagacc tagattcaaa ctcagatgac tttgaccctg cttccaccaa gagcaagtat    2460
gactctctgg attttgatag tttactgaaa gaagctcaga gaagcttgcg caggtaacat    2520
gttccctagc tgaggatgac agagggatgg cgaatacctc atgggacagc gcgtccttcc    2580
ctaaagacta ttgcaagtca tacttaggaa tttctcctac tttacactct ctgtacaaaa    2640
acaaaacaaa acaacaacaa tacaacaaga acaacaacaa caataacaac aatggtttac    2700
atgaacacag ctgctgaaga ggcaagagac agaatgatat ccagtaagca catgtttatt    2760
catgggtgtc agctttgctt ttcctggagt ctcttggtga tggagtgtgc gtgtgtgcat    2820
gtatgtgtgt gtgtatgtat gtgtgtggtg tgtgtgcttg gtttagggga agtatgtgtg    2880
ggtacatgtg aggactgggg gcacctgacc agaatgcgca agggcaaacc atttcaaatg    2940
gcagcagttc catgaagaca cgcttaaaac ctagaacttc aaaatgttcg tattctattc    3000
aaaaggaaat atatatatat atatatatat atatatatat atatataaat taaaaaggaa    3060
agaaaactaa caaccaacca accaaccaac caaccacaaa ccaccctaaa atgacagccg    3120
ctgatgtctg ggcatcagcc tttgtactct gtttttttaa gaaagtgcag aatcaacttg    3180
aagcaagctt tctctcataa cgtaatgatt atatgacaat cctgaagaaa ccacaggttc    3240
catagaacta atatcctgtc tctctctctc tctctctctc tctctttttt ttttcttttt    3300
ccttttgcca tggaatctgg gtgggagagg atactgcggg caccagaatg ctaaagtttc    3360
ctaacatttt gaagtttctg tagttcatcc ttaatcctga cacccatgta aatgtccaaa    3420
atgttgatct tccactgcaa atttcaaaag ccttgtcaat ggtcaagcgt gcagcttgtt    3480
cagcggttct ttctgaggag cggacaccgg gttacattac taatgagagt tgggtagaac    3540
```

```
tctctgagat gtgttcagat agtgtaattg ctacattctc tgatgtagtt aagtatttac    3600
agatgttaaa tggagtattt ttattttatg tatatactat acaacaatgt tctttttgt     3660 tacagctatg cactgtaaat gcagccttct tttcaaaact gctaaatttt tcttaatcaa    3720
gaatattcaa atgtaattat gaggtgaaac aattattgta cactaacata tttagaagct    3780
gaacttactg cttatatata tttgattgta aaaacaaaaa gacagtgtgt gtgtctgttg    3840
agtgcaacaa gagcaaaatg atgctttccg cacatccatc ccttaggtga gcttcaatct    3900
aagcatcttg tcaagaaata tcctagtccc ctaaaggtat taaccacttc tgcgatattt    3960
ttccacattt tcttgtcgct tgttttctt tgaagtttta tacactggat ttgttagggg     4020
aatgaaattt tctcatctaa aattttcta aagatatca tgatttatg taaagtctct       4080 caatgggtaa ccattaagaa atgtttttat tttctctatc aacagtagtt ttgaaactag    4140
aagtcaaaaa tcttttaaa atgctgtttt gttttaattt ttgtgatttt aatttgatac     4200
aaaatgctga ggtaataatt atagtatgat ttttacaata attaatgtgt gtctgaagac    4260
tatctttgaa gccagtattt cttttccttg gcagagtatg acgatggtat ttatctgtat    4320
tttttacagt tatgcatcct gtataaatac tgatatttca ttccttgtt tactaaagag     4380 acatatttat cagttgcaga tagcctattt attataaatt atgagatgat gaaaataata    4440
aagccagtgg aaattttcta cctaggatgc atgacaattg tcaggttgga gtgtaagtgc    4500
ttcatttggg aaattcagct tttgcagaag cagtgtttct acttgcacta gcatggcctc    4560
tgacgtgacc atggtgttgt tcttgatgac attgcttctg ctaaatttaa taaaaacttc    4620
agaaaaacct ccatttttgat catcaggatt tcatctgagt gtggagtccc tggaatggaa   4680
ttcagtaaca tttggagtgt gtattcaagt ttctaaattg agattcgatt actgtttggc    4740
tgacatgact tttctggaag acatgataca cctactactc aattgttctt ttccttcttc    4800
tcgcccaaca cgatcttgta agatggattt cacccccagg ccaatgcagc taattttgat    4860
agctgcattc atttatcacc agcatattgt gttctgagtg aatccactgt ttgtcctgtc    4920
ggatgcttgc ttgattttt ggcttcttat ttctaagtag atagaaagca ataaaaatac     4980
tatgaaatga agaacttgt tcacaggttc tgcgttacaa cagtaacaca tctttaatcc    5040
gcctaattct tgttgttctg taggttaaat gcaggtattt taactgtgtg aacgccaaac    5100
taaagtttac agtctttctt tctgaatttt gagtatcttc tgttgtagaa taataataaa    5160
aagactatta agagcaataa attattttta agaaatcgag atttagtaaa tcctattatg    5220
tgttcaagga ccacatgtgt tctctatttt gcctttaaat ttttgtgaac caattttaaa    5280
tacattctcc ttttgccct ggattgttga catgagtgga atacttggtt tcttttctta    5340
cttatcaaaa gacagcacta cagatatcat attgaggatt aatttatccc cctacccc     5400 agcctgacaa atattgttac catgaagata gttttcctca atggacttca aattgcatct    5460
agaattagtg gagcttttgt atcttctgca gacactgtgg gtagcccatc aaaatgtaag    5520
ctgtgctcct ctcatttta ttttatttt tttgggagag aatatttcaa atgaacacgt      5580
gcaccccatc atcactggag gcaaatttca gcatagatct gtaggatttt tagaagaccg    5640
tgggccattg ccttcatgcc gtggtaagta ccacatctac aatttggta accgaactgg     5700 tgctttagta atgtggattt ttttctttt taaaagagat gtagcagaat aattcttcca     5760
gtgcaacaaa atcaattttt tgctaaacga ctccgagaac aacagttggg ctgtcaacat    5820
tcaaagcagc agagagggaa ctttgcacta ttggggtatg atgtttgggt cagttgataa    5880
```

-continued

```
aaggaaacct tttcatgcct ttagatgtga gcttccagta ggtaatgatt atgtgtcctt    5940
tcttgatggc tgtaatgaga acttcaatca ctgtagtcta agacctgatc tatagatgac    6000
ctagaatagc catgtactat aatgtgatga ttctaaattt gtacctatgt gacagacatt    6060
ttcaataatg tgaactgctg atttgatgga gctactttaa gatttgtagg tgaaagtgta    6120
atactgttgg ttgaactatg ctgaagaggg aaagtgagcg attagttgag cccttgccgg    6180
gccttttttc cacctgccaa ttctacatgt attgttgtgg ttttattcat tgtatgaaaa    6240
ttcctgtgat ttttttttaaa tgtgcagtac acatcagcct cactgagcta ataaagggaa    6300
acgaatgttt caaatct                                                    6317
```

<210> SEQ ID NO 3
<211> LENGTH: 3030
<212> TYPE: DNA
<213> ORGANISM: Homo sapiens
<220> FEATURE:
<221> NAME/KEY: CDS
<222> LOCATION: (1)...(3027)

<400> SEQUENCE: 3

```
atg cct cct gtg tat gcc tct gag tat gtc ttg cca ctc cag ggt gga    48
Met Pro Pro Val Tyr Ala Ser Glu Tyr Val Leu Pro Leu Gln Gly Gly
  1               5                  10                  15 ggg tcc ggg gag gag caa ctc tat gct gac ttt cca gaa ctc gac ctc    96
Gly Ser Gly Glu Glu Gln Leu Tyr Ala Asp Phe Pro Glu Leu Asp Leu
             20                  25                  30 tcc cag ctg gat gcc agc gac ttt gac tcg gcc acc tgc ttt ggg gag   144
Ser Gln Leu Asp Ala Ser Asp Phe Asp Ser Ala Thr Cys Phe Gly Glu
         35                  40                  45 ctg cag tgg tgc cca gag aac tca gag act gaa ccc aac cag tac agc   192
Leu Gln Trp Cys Pro Glu Asn Ser Glu Thr Glu Pro Asn Gln Tyr Ser
     50                  55                  60 ccc gat gac tcc gag ctc ttc cag att gac agt gag aat gag gcc ctc   240
Pro Asp Asp Ser Glu Leu Phe Gln Ile Asp Ser Glu Asn Glu Ala Leu
 65                  70                  75                  80 ctg gca gag ctc acc aag acc ctg gat gac atc cct gaa gat gac gtg   288
Leu Ala Glu Leu Thr Lys Thr Leu Asp Asp Ile Pro Glu Asp Asp Val
                 85                  90                  95 ggt ctg gct gcc ttc cca gcc ctg gat ggt gga gac gct cta tca tgc   336
Gly Leu Ala Ala Phe Pro Ala Leu Asp Gly Gly Asp Ala Leu Ser Cys
            100                 105                 110 acc tca gct tcg cct gcc ccc tca tct gca ccc ccc agc cct gcc ccg   384
Thr Ser Ala Ser Pro Ala Pro Ser Ser Ala Pro Pro Ser Pro Ala Pro
        115                 120                 125 gag aag ccc tcg gcc cca gcc cct gag gtg gac gag ctc tca ctg ctg   432
Glu Lys Pro Ser Ala Pro Ala Pro Glu Val Asp Glu Leu Ser Leu Leu
    130                 135                 140 cag aag ctc ctc ctg gcc aca tcc tac cca aca tca agc tct gac acc   480
Gln Lys Leu Leu Leu Ala Thr Ser Tyr Pro Thr Ser Ser Ser Asp Thr
145                 150                 155                 160 cag aag gaa ggg acc gcc tgg cgc cag gca ggc ctc aga tct aaa agt   528
Gln Lys Glu Gly Thr Ala Trp Arg Gln Ala Gly Leu Arg Ser Lys Ser
                165                 170                 175 caa cgg cct tgt gtt aag gcg gac agc acc caa gac aag aag gct ccc   576
Gln Arg Pro Cys Val Lys Ala Asp Ser Thr Gln Asp Lys Lys Ala Pro
            180                 185                 190 atg atg cag tct cag agc cga agt tgt aca gaa cta cat aag cac ctc   624
Met Met Gln Ser Gln Ser Arg Ser Cys Thr Glu Leu His Lys His Leu
        195                 200                 205
```

```
acc tcg gca cag tgc tgc ctg cag gat cgg ggt ctg cag cca cca tgc      672
Thr Ser Ala Gln Cys Cys Leu Gln Asp Arg Gly Leu Gln Pro Pro Cys
    210             215                 220 ctc cag agt ccc cgg ctc cct gcc aag gag gac aag gag ccg ggt gag      720
Leu Gln Ser Pro Arg Leu Pro Ala Lys Glu Asp Lys Glu Pro Gly Glu
225             230                 235                 240 gac tgc ccg agc ccc cag cca gct cca gcc tct ccc cgg gac tcc cta      768
Asp Cys Pro Ser Pro Gln Pro Ala Pro Ala Ser Pro Arg Asp Ser Leu
                    245                 250                 255 gct ctg ggc agg gca gac ccc ggt gcc ccg gtt tcc cag gaa gac atg      816
Ala Leu Gly Arg Ala Asp Pro Gly Ala Pro Val Ser Gln Glu Asp Met
                260                 265                 270 cag gcg atg gtg caa ctc ata cgc tac atg cac acc tac tgc ctc ccc      864
Gln Ala Met Val Gln Leu Ile Arg Tyr Met His Thr Tyr Cys Leu Pro
            275                 280                 285 cag agg aag ctg ccc cca cag acc cct gag cca ctc ccc aag gcc tgc      912
Gln Arg Lys Leu Pro Pro Gln Thr Pro Glu Pro Leu Pro Lys Ala Cys
        290                 295                 300 agc aac ccc tcc cag cag gtc aga tcc cgg ccc tgg tcc cgg cac cac      960
Ser Asn Pro Ser Gln Gln Val Arg Ser Arg Pro Trp Ser Arg His His
305                 310                 315                 320 tcc aaa gcc tcc tgg gct gag ttc tcc att ctg agg gaa ctt ctg gct     1008
Ser Lys Ala Ser Trp Ala Glu Phe Ser Ile Leu Arg Glu Leu Leu Ala
                325                 330                 335 caa gac gtg ctc tgt gat gtc agc aaa ccc tac cgt ctg gcc acg cct     1056
Gln Asp Val Leu Cys Asp Val Ser Lys Pro Tyr Arg Leu Ala Thr Pro
            340                 345                 350 gtt tat gcc tcc ctc aca cct cgg tca agg ccc agg ccc ccc aaa gac     1104
Val Tyr Ala Ser Leu Thr Pro Arg Ser Arg Pro Arg Pro Pro Lys Asp
        355                 360                 365 agt cag gcc tcc cct ggt cgc cca tcc tcg gtg gag gag gta agg atc     1152
Ser Gln Ala Ser Pro Gly Arg Pro Ser Ser Val Glu Glu Val Arg Ile
370                 375                 380 gca gct tca ccc aag agc acc ggg ccc aga cca agc ctg cgc cca ctg     1200
Ala Ala Ser Pro Lys Ser Thr Gly Pro Arg Pro Ser Leu Arg Pro Leu
385                 390                 395                 400 cgg ctg gag gtg aaa agg gag gtc cgc cgg cct gcc aga ctg cag cag     1248
Arg Leu Glu Val Lys Arg Glu Val Arg Arg Pro Ala Arg Leu Gln Gln
                405                 410                 415 cag gag gag gaa gac gag gaa gaa gag gag gaa gag gaa gaa gaa         1296
Gln Glu Glu Glu Asp Glu Glu Glu Glu Glu Glu Glu Glu Glu Glu
            420                 425                 430 aaa gag gag gag gag gag tgg ggc agg aaa agg cca ggc cga ggc ctg     1344
Lys Glu Glu Glu Glu Glu Trp Gly Arg Lys Arg Pro Gly Arg Gly Leu
        435                 440                 445 cca tgg acg aag ctg ggg agg aag ctg gag agc tct gtg tgc ccc gtg     1392
Pro Trp Thr Lys Leu Gly Arg Lys Leu Glu Ser Ser Val Cys Pro Val
    450                 455                 460 cgg cgt tct cgg aga ctg aac cct gag ctg ggc ccc tgg ctg aca ttt     1440
Arg Arg Ser Arg Arg Leu Asn Pro Glu Leu Gly Pro Trp Leu Thr Phe
465                 470                 475                 480 gca gat gag ccg ctg gtc ccc tcg gag ccc caa ggt gct ctg ccc tca     1488
Ala Asp Glu Pro Leu Val Pro Ser Glu Pro Gln Gly Ala Leu Pro Ser
                485                 490                 495 ctg tgc ctg gct ccc aag gcc tac gac gta gag cgg gag ctg ggc agc     1536
Leu Cys Leu Ala Pro Lys Ala Tyr Asp Val Glu Arg Glu Leu Gly Ser
            500                 505                 510 ccc acg gac gag gac agt ggc caa gac cag cag ctc cta cgg gga ccc     1584
Pro Thr Asp Glu Asp Ser Gly Gln Asp Gln Gln Leu Leu Arg Gly Pro
        515                 520                 525
```

```
cag atc cct gcc ctg gag agc ccc tgt gag agt ggc gac cca act ttt       1632
Gln Ile Pro Ala Leu Glu Ser Pro Cys Glu Ser Gly Asp Pro Thr Phe
    530                 535                 540 ggc aag aag agc ttt gag cag acc ttg aca gtg gag ctc tgt ggc aca       1680
Gly Lys Lys Ser Phe Glu Gln Thr Leu Thr Val Glu Leu Cys Gly Thr
545                 550                 555                 560 gca ggt gag cca ggg ggc ttc cac tgg cag gtg cct tca gga aaa cac       1728
Ala Gly Glu Pro Gly Gly Phe His Trp Gln Val Pro Ser Gly Lys His
                565                 570                 575 ccg tgc atc tct gag ttt ttc atc atg cat ggg caa gga ctc acc cca       1776
Pro Cys Ile Ser Glu Phe Phe Ile Met His Gly Gln Gly Leu Thr Pro
            580                 585                 590 ccc acc aca cca ccg tac aag ccc aca gag gag gat ccc ttc aaa cca       1824
Pro Thr Thr Pro Pro Tyr Lys Pro Thr Glu Glu Asp Pro Phe Lys Pro
        595                 600                 605 gac atc aag cat agt cta ggc aaa gaa ata gct ctc agc ctc ccc tcc       1872
Asp Ile Lys His Ser Leu Gly Lys Glu Ile Ala Leu Ser Leu Pro Ser
    610                 615                 620 cct gag ggc ctc tca ctc aag gcc acc cca ggg gct gcc cac aag ctg       1920
Pro Glu Gly Leu Ser Leu Lys Ala Thr Pro Gly Ala Ala His Lys Leu
625                 630                 635                 640 cca aag aag cac cca gag cga agt gag ctc ctg tcc cac ctg cga cat       1968
Pro Lys Lys His Pro Glu Arg Ser Glu Leu Leu Ser His Leu Arg His
                645                 650                 655 gcc aca gcc cag cca gcc tcc cag gct ggc cag aag cgt ccc ttc tcc       2016
Ala Thr Ala Gln Pro Ala Ser Gln Ala Gly Gln Lys Arg Pro Phe Ser
            660                 665                 670 tgt tcc ttt gga gac cat gac tac tgc cag gtg ctc cga cca gaa ggc       2064
Cys Ser Phe Gly Asp His Asp Tyr Cys Gln Val Leu Arg Pro Glu Gly
        675                 680                 685 gtc ctg caa agg aag gtg ctg agg tcc tgg gag ccg tct ggg gtt cac       2112
Val Leu Gln Arg Lys Val Leu Arg Ser Trp Glu Pro Ser Gly Val His
    690                 695                 700 ctt gag gac tgg ccc cag cag ggt gcc cct tgg gct gag gca cag gcc       2160
Leu Glu Asp Trp Pro Gln Gln Gly Ala Pro Trp Ala Glu Ala Gln Ala
705                 710                 715                 720 cct ggc agg gag gaa gac aga agc tgt gat gct ggc gcc cca ccc aag       2208
Pro Gly Arg Glu Glu Asp Arg Ser Cys Asp Ala Gly Ala Pro Pro Lys
                725                 730                 735 gac agc acg ctg ctg aga gac cat gag atc cgt gcc agc ctc acc aaa       2256
Asp Ser Thr Leu Leu Arg Asp His Glu Ile Arg Ala Ser Leu Thr Lys
            740                 745                 750 cac ttt ggg ctg ctg gag acc gcc ctg gag gag gaa gac ctg gcc tcc       2304
His Phe Gly Leu Leu Glu Thr Ala Leu Glu Glu Glu Asp Leu Ala Ser
        755                 760                 765 tgc aag agc cct gag tat gac act gtc ttt gaa gac agc agc agc agc       2352
Cys Lys Ser Pro Glu Tyr Asp Thr Val Phe Glu Asp Ser Ser Ser Ser
    770                 775                 780 agc ggc gag agc agc ttc ctc cca gag gag gaa gag gaa ggg gag           2400
Ser Gly Glu Ser Ser Phe Leu Pro Glu Glu Glu Glu Glu Glu Gly Glu
785                 790                 795                 800 gag gag gag gag gac gat gaa gaa gag gac tca ggg gtc agc ccc act       2448
Glu Glu Glu Glu Asp Asp Glu Glu Glu Asp Ser Gly Val Ser Pro Thr
                805                 810                 815 tgc tct gac cac tgc ccc tac cag agc cca cca agc aag gcc aac cgg       2496
Cys Ser Asp His Cys Pro Tyr Gln Ser Pro Pro Ser Lys Ala Asn Arg
            820                 825                 830 cag ctc tgt tcc cgc agc cgc tca agc tct ggc tct tca ccc tgc cac       2544
Gln Leu Cys Ser Arg Ser Arg Ser Ser Gly Ser Ser Pro Cys His
```

-continued

```
                835                 840                 845
tcc tgg tca cca gcc act cga agg aac ttc aga tgt gag agc aga ggg      2592
Ser Trp Ser Pro Ala Thr Arg Arg Asn Phe Arg Cys Glu Ser Arg Gly
    850                 855                 860 ccg tgt tca gac aga acg cca agc atc cgg cac gcc agg aag cgg cgg      2640
Pro Cys Ser Asp Arg Thr Pro Ser Ile Arg His Ala Arg Lys Arg Arg
865                 870                 875                 880 gaa aag gcc att ggg gaa ggc cgc gtg gtg tac att caa aat ctc tcc      2688
Glu Lys Ala Ile Gly Glu Gly Arg Val Val Tyr Ile Gln Asn Leu Ser
                885                 890                 895 agc gac atg agc tcc cga gag ctg aag agg cgc ttt gaa gtg ttt ggt      2736
Ser Asp Met Ser Ser Arg Glu Leu Lys Arg Arg Phe Glu Val Phe Gly
            900                 905                 910 gag att gag gag tgc gag gtg ctg aca aga aat agg aga ggc gag aag      2784
Glu Ile Glu Glu Cys Glu Val Leu Thr Arg Asn Arg Arg Gly Glu Lys
        915                 920                 925 tac ggc ttc atc acc tac cgg tgt tct gag cac gcg gcc ctc tct ttg      2832
Tyr Gly Phe Ile Thr Tyr Arg Cys Ser Glu His Ala Ala Leu Ser Leu
    930                 935                 940 aca aag ggc gct gcc ctg agg aag cgc aac gag ccc tcc ttc cag ctg      2880
Thr Lys Gly Ala Ala Leu Arg Lys Arg Asn Glu Pro Ser Phe Gln Leu
945                 950                 955                 960 agc tac gga ggg ctc cgg cac ttc tgc tgg ccc aga tac act gac tac      2928
Ser Tyr Gly Gly Leu Arg His Phe Cys Trp Pro Arg Tyr Thr Asp Tyr
                965                 970                 975 gat tcc aat tca gaa gag gcc ctt cct gcg tca ggg aaa agc aag tat      2976
Asp Ser Asn Ser Glu Glu Ala Leu Pro Ala Ser Gly Lys Ser Lys Tyr
            980                 985                 990 gaa gcc atg gat ttt gac agc tta ctg aaa gag gcc cag cag agc ctg      3024
Glu Ala Met Asp Phe Asp Ser Leu Leu Lys Glu Ala Gln Gln Ser Leu
        995                 1000                1005 cat tga                                                              3030
His

<210> SEQ ID NO 4
<211> LENGTH: 797
<212> TYPE: PRT
<213> ORGANISM: Homo sapiens

<400> SEQUENCE: 4

Met Ala Trp Asp Met Cys Ser Gln Asp Ser Val Trp Ser Asp Ile Glu
1               5                   10                  15

Cys Ala Ala Leu Val Gly Glu Asp Gln Pro Leu Cys Pro Asp Leu Pro
            20                  25                  30

Glu Leu Asp Leu Ser Glu Leu Asp Val Asn Asp Leu Asp Thr Asp Ser
        35                  40                  45

Phe Leu Gly Gly Leu Lys Trp Cys Ser Asp Gln Ser Glu Ile Ile Ser
    50                  55                  60

Asn Gln Tyr Asn Asn Glu Pro Ala Asn Ile Phe Glu Lys Ile Asp Glu
65                  70                  75                  80

Glu Asn Glu Ala Asn Leu Leu Ala Val Leu Thr Glu Thr Leu Asp Ser
                85                  90                  95

Leu Pro Val Asp Glu Asp Gly Leu Pro Ser Phe Asp Ala Leu Thr Asp
            100                 105                 110

Gly Ala Val Thr Thr Asp Asn Glu Ala Ser Pro Ser Ser Met Pro Asp
        115                 120                 125

Gly Thr Pro Pro Pro Gln Glu Ala Glu Glu Pro Ser Leu Leu Lys Lys
    130                 135                 140
```

```
Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Lys Pro Gln Arg Arg Pro Cys Ser Glu
        195                 200                 205

Leu Leu Lys Tyr Leu Thr Thr Asn Asp Asp Pro Pro His Thr Lys Pro
        210                 215                 220

Thr Glu Asn Arg Asn Ser Ser Arg Asp Lys Cys Ala Ser Lys Lys Lys
225                 230                 235                 240

Ser His Thr Gln Pro Gln Ser Gln His Ala Gln Ala Lys Pro Thr Thr
                245                 250                 255

Leu Ser Leu Pro Leu Thr Pro Glu Ser Pro Asn Asp Pro Lys Gly Ser
                260                 265                 270

Pro Phe Glu Asn Lys Thr Ile Glu Arg Thr Leu Ser Val Glu Leu Ser
        275                 280                 285

Gly Thr Ala Gly Leu Thr Pro Pro Thr Thr Pro His Lys Ala Asn
290                 295                 300

Gln Asp Asn Pro Phe Lys Ala Ser Pro Lys Leu Lys Pro Ser Cys Lys
305                 310                 315                 320

Thr Val Val Pro Pro Thr Lys Arg Ala Arg Tyr Ser Glu Cys Ser
                325                 330                 335

Gly Thr Gln Gly Ser His Ser Thr Lys Lys Gly Pro Glu Gln Ser Glu
                340                 345                 350

Leu Tyr Ala Gln Leu Ser Lys Ser Ser Gly Leu Ser Arg Gly His Glu
        355                 360                 365

Glu Arg Lys Thr Lys Arg Pro Ser Leu Arg Leu Phe Gly Asp His Asp
        370                 375                 380

Tyr Cys Gln Ser Leu Asn Ser Lys Thr Asp Ile Leu Ile Asn Ile Ser
385                 390                 395                 400

Gln Glu Leu Gln Asp Ser Arg Gln Leu Asp Phe Lys Asp Ala Ser Cys
                405                 410                 415

Asp Trp Gln Gly His Ile Cys Ser Ser Thr Asp Ser Gly Gln Cys Tyr
            420                 425                 430

Leu Arg Glu Thr Leu Glu Ala Ser Lys Gln Val Ser Pro Cys Ser Thr
        435                 440                 445

Arg Lys Gln Leu Gln Asp Gln Glu Ile Arg Ala Glu Leu Asn Lys His
    450                 455                 460

Phe Gly His Pro Cys Gln Ala Val Phe Asp Asp Lys Ser Asp Lys Thr
465                 470                 475                 480

Ser Glu Leu Arg Asp Gly Asp Phe Ser Asn Glu Gln Phe Ser Lys Leu
                485                 490                 495

Pro Val Phe Ile Asn Ser Gly Leu Ala Met Asp Gly Leu Phe Asp Asp
            500                 505                 510

Ser Glu Asp Glu Ser Asp Lys Leu Ser Tyr Pro Trp Asp Gly Thr Gln
        515                 520                 525

Pro Tyr Ser Leu Phe Asp Val Ser Pro Cys Ser Ser Phe Asn Ser
        530                 535                 540

Pro Cys Arg Asp Ser Val Ser Pro Pro Lys Ser Leu Phe Ser Gln Arg
545                 550                 555                 560
```

Pro Gln Arg Met Arg Ser Arg Ser Arg Ser Phe Ser Arg His Arg Ser
            565                 570                 575

Cys Ser Arg Ser Pro Tyr Ser Arg Ser Arg Ser Arg Ser Pro Gly Ser
            580                 585                 590

Arg Ser Ser Ser Arg Ser Cys Tyr Tyr Tyr Glu Ser Ser His Tyr Arg
            595                 600                 605

His Arg Thr His Arg Asn Ser Pro Leu Tyr Val Arg Ser Arg Ser Arg
    610                 615                 620

Ser Pro Tyr Ser Arg Arg Pro Arg Tyr Asp Ser Tyr Glu Ala Tyr Glu
625                 630                 635                 640

His Glu Arg Leu Lys Arg Asp Glu Tyr Arg Lys Glu His Glu Lys Arg
                645                 650                 655

Glu Ser Glu Arg Ala Lys Gln Arg Glu Arg Gln Lys Gln Lys Ala Ile
            660                 665                 670

Glu Glu Arg Arg Val Ile Tyr Val Gly Lys Ile Arg Pro Asp Thr Thr
            675                 680                 685

Arg Thr Glu Leu Arg Asp Arg Phe Glu Val Phe Gly Glu Ile Glu Glu
    690                 695                 700

Cys Thr Val Asn Leu Arg Asp Asp Gly Asp Ser Tyr Gly Phe Ile Thr
705                 710                 715                 720

Tyr Arg Tyr Thr Cys Asp Ala Phe Ala Ala Leu Glu Asn Gly Tyr Thr
                725                 730                 735

Leu Arg Arg Ser Asn Glu Thr Asp Phe Glu Leu Tyr Phe Cys Gly Arg
            740                 745                 750

Lys Gln Phe Phe Lys Ser Asn Tyr Ala Asp Leu Asp Thr Asn Ser Asp
            755                 760                 765

Asp Phe Asp Pro Ala Ser Thr Lys Ser Lys Tyr Asp Ser Leu Asp Phe
    770                 775                 780

Asp Ser Leu Leu Lys Glu Ala Gln Arg Ser Leu Arg Arg
785                 790                 795

<210> SEQ ID NO 5
<211> LENGTH: 798
<212> TYPE: PRT
<213> ORGANISM: Homo sapiens

<400> SEQUENCE: 5

Met Ala Trp Asp Met Cys Asn Gln Asp Ser Glu Ser Val Trp Ser Asp
1               5                   10                  15

Ile Glu Cys Ala Ala Leu Val Gly Glu Asp Gln Pro Leu Cys Pro Asp
            20                  25                  30

Leu Pro Glu Leu Asp Leu Ser Glu Leu Asp Val Asn Asp Leu Asp Thr
        35                  40                  45

Asp Ser Phe Leu Gly Gly Leu Lys Trp Cys Ser Asp Gln Ser Glu Ile
    50                  55                  60

Ile Ser Asn Gln Tyr Asn Asn Glu Pro Ser Asn Ile Phe Glu Lys Ile
65                  70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Gln Glu Ala Glu Glu Pro Ser Leu Leu
    130                 135                 140

```
Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
            165                 170                 175

Arg Thr Asn Pro Ala Ile Val Lys Thr Glu Asn Ser Trp Ser Asn Lys
        180                 185                 190

Ala Lys Ser Ile Cys Gln Gln Lys Pro Gln Arg Arg Pro Cys Ser
    195                 200                 205

Glu Leu Leu Lys Tyr Leu Thr Thr Asn Asp Asp Pro Pro His Thr Lys
    210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Thr Thr Pro Pro His Lys Ala
    290                 295                 300

Asn Gln Asp Asn Pro Phe Arg Ala Ser Pro Lys Leu Lys Ser Ser Cys
305                 310                 315                 320

Lys Thr Val Val Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
                405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
450                 455                 460

His Phe Gly His Pro Ser Gln Ala Val Phe Asp Asp Glu Ala Asp Lys
465                 470                 475                 480

Thr Gly Glu Leu Arg Asp Ser Asp Phe Ser Asn Glu Gln Phe Ser Lys
                485                 490                 495

Leu Pro Met Phe Ile Asn Ser Gly Leu Ala Met Asp Gly Leu Phe Asp
            500                 505                 510

Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
    530                 535                 540

Ser Pro Cys Arg Asp Ser Val Ser Pro Pro Lys Ser Leu Phe Ser Gln
545                 550                 555                 560
```

Arg Pro Gln Arg Met Arg Ser Arg Ser Arg Ser Phe Ser Arg His Arg
                565                 570                 575

Ser Cys Ser Arg Ser Pro Tyr Ser Arg Ser Arg Ser Arg Ser Pro Gly
                580                 585                 590

Ser Arg Ser Ser Ser Arg Ser Cys Tyr Tyr Tyr Glu Ser Ser His Tyr
                595                 600                 605

Arg His Arg Thr His Arg Asn Ser Pro Leu Tyr Val Arg Ser Arg Ser
                610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
                645                 650                 655

Arg Glu Ser Glu Arg Ala Lys Gln Arg Glu Arg Gln Arg Gln Lys Ala
                660                 665                 670

Ile Glu Glu Arg Arg Val Ile Tyr Val Gly Lys Ile Arg Pro Asp Thr
                675                 680                 685

Thr Arg Thr Glu Leu Arg Asp Arg Phe Glu Val Phe Gly Glu Ile Glu
690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
                740                 745                 750

Arg Lys Gln Phe Phe Lys Ser Asn Tyr Ala Asp Leu Asp Ser Asn Ser
                755                 760                 765

Asp Asp Phe Asp Pro Ala Ser Thr Lys Ser Lys Tyr Asp Ser Leu Asp
                770                 775                 780

Phe Asp Ser Leu Leu Lys Glu Ala Gln Arg Ser Leu Arg Arg
785                 790                 795

<210> SEQ ID NO 6
<211> LENGTH: 1009
<212> TYPE: PRT
<213> ORGANISM: Homo sapiens

<400> SEQUENCE: 6

Met Pro Pro Val Tyr Ala Ser Glu Tyr Val Leu Pro Leu Gln Gly Gly
1               5                   10                  15

Gly Ser Gly Glu Glu Gln Leu Tyr Ala Asp Phe Pro Glu Leu Asp Leu
                20                  25                  30

Ser Gln Leu Asp Ala Ser Asp Phe Asp Ser Ala Thr Cys Phe Gly Glu
                35                  40                  45

Leu Gln Trp Cys Pro Glu Asn Ser Glu Thr Glu Pro Asn Gln Tyr Ser
        50                  55                  60

Pro Asp Asp Ser Glu Leu Phe Gln Ile Asp Ser Glu Asn Glu Ala Leu
65                  70                  75                  80

Leu Ala Glu Leu Thr Lys Thr Leu Asp Asp Ile Pro Glu Asp Asp Val
                85                  90                  95

Gly Leu Ala Ala Phe Pro Ala Leu Asp Gly Gly Asp Ala Leu Ser Cys
                100                 105                 110

Thr Ser Ala Ser Pro Ala Pro Ser Ser Ala Pro Pro Ser Pro Ala Pro
                115                 120                 125

Glu Lys Pro Ser Ala Pro Ala Pro Glu Val Asp Glu Leu Ser Leu Leu
                130                 135                 140

-continued

```
Gln Lys Leu Leu Leu Ala Thr Ser Tyr Pro Thr Ser Ser Ser Asp Thr
145                 150                 155                 160

Gln Lys Glu Gly Thr Ala Trp Arg Gln Ala Gly Leu Arg Ser Lys Ser
                165                 170                 175

Gln Arg Pro Cys Val Lys Ala Asp Ser Thr Gln Asp Lys Lys Ala Pro
            180                 185                 190

Met Met Gln Ser Gln Ser Arg Ser Cys Thr Glu Leu His Lys His Leu
        195                 200                 205

Thr Ser Ala Gln Cys Cys Leu Gln Asp Arg Gly Leu Gln Pro Pro Cys
    210                 215                 220

Leu Gln Ser Pro Arg Leu Pro Ala Lys Glu Asp Lys Glu Pro Gly Glu
225                 230                 235                 240

Asp Cys Pro Ser Pro Gln Pro Ala Pro Ala Ser Pro Arg Asp Ser Leu
                245                 250                 255

Ala Leu Gly Arg Ala Asp Pro Gly Ala Pro Val Ser Gln Glu Asp Met
            260                 265                 270

Gln Ala Met Val Gln Leu Ile Arg Tyr Met His Thr Tyr Cys Leu Pro
        275                 280                 285

Gln Arg Lys Leu Pro Pro Gln Thr Pro Glu Pro Leu Pro Lys Ala Cys
    290                 295                 300

Ser Asn Pro Ser Gln Gln Val Arg Ser Arg Pro Trp Ser Arg His His
305                 310                 315                 320

Ser Lys Ala Ser Trp Ala Glu Phe Ser Ile Leu Arg Glu Leu Leu Ala
                325                 330                 335

Gln Asp Val Leu Cys Asp Val Ser Lys Pro Tyr Arg Leu Ala Thr Pro
            340                 345                 350

Val Tyr Ala Ser Leu Thr Pro Arg Ser Arg Pro Arg Pro Lys Asp
        355                 360                 365

Ser Gln Ala Ser Pro Gly Arg Pro Ser Ser Val Glu Glu Val Arg Ile
    370                 375                 380

Ala Ala Ser Pro Lys Ser Thr Gly Pro Arg Pro Ser Leu Arg Pro Leu
385                 390                 395                 400

Arg Leu Glu Val Lys Arg Glu Val Arg Arg Pro Ala Arg Leu Gln Gln
                405                 410                 415

Gln Glu Glu Glu Asp Glu Glu Glu Glu Glu Glu Glu Glu Glu Glu Glu
            420                 425                 430

Lys Glu Glu Glu Glu Glu Trp Gly Arg Lys Arg Pro Gly Arg Gly Leu
        435                 440                 445

Pro Trp Thr Lys Leu Gly Arg Lys Leu Glu Ser Ser Val Cys Pro Val
    450                 455                 460

Arg Arg Ser Arg Arg Leu Asn Pro Glu Leu Gly Pro Trp Leu Thr Phe
465                 470                 475                 480

Ala Asp Glu Pro Leu Val Pro Ser Glu Pro Gln Gly Ala Leu Pro Ser
                485                 490                 495

Leu Cys Leu Ala Pro Lys Ala Tyr Asp Val Glu Arg Glu Leu Gly Ser
            500                 505                 510

Pro Thr Asp Glu Asp Ser Gly Gln Asp Gln Gln Leu Leu Arg Gly Pro
        515                 520                 525

Gln Ile Pro Ala Leu Glu Ser Pro Cys Glu Ser Gly Asp Pro Thr Phe
    530                 535                 540

Gly Lys Lys Ser Phe Glu Gln Thr Leu Thr Val Glu Leu Cys Gly Thr
545                 550                 555                 560
```

-continued

Ala Gly Glu Pro Gly Gly Phe His Trp Gln Val Pro Ser Gly Lys His
              565                 570                 575

Pro Cys Ile Ser Glu Phe Phe Ile Met His Gly Gln Gly Leu Thr Pro
              580                 585                 590

Pro Thr Thr Pro Pro Tyr Lys Pro Thr Glu Glu Asp Pro Phe Lys Pro
              595                 600                 605

Asp Ile Lys His Ser Leu Gly Lys Glu Ile Ala Leu Ser Leu Pro Ser
        610                 615                 620

Pro Glu Gly Leu Ser Leu Lys Ala Thr Pro Gly Ala Ala His Lys Leu
625                 630                 635                 640

Pro Lys Lys His Pro Glu Arg Ser Glu Leu Leu Ser His Leu Arg His
                645                 650                 655

Ala Thr Ala Gln Pro Ala Ser Gln Ala Gly Gln Lys Arg Pro Phe Ser
                660                 665                 670

Cys Ser Phe Gly Asp His Asp Tyr Cys Gln Val Leu Arg Pro Glu Gly
            675                 680                 685

Val Leu Gln Arg Lys Val Leu Arg Ser Trp Glu Pro Ser Gly Val His
        690                 695                 700

Leu Glu Asp Trp Pro Gln Gln Gly Ala Pro Trp Ala Glu Ala Gln Ala
705                 710                 715                 720

Pro Gly Arg Glu Glu Asp Arg Ser Cys Asp Ala Gly Ala Pro Pro Lys
                725                 730                 735

Asp Ser Thr Leu Leu Arg Asp His Glu Ile Arg Ala Ser Leu Thr Lys
                740                 745                 750

His Phe Gly Leu Leu Glu Thr Ala Leu Glu Glu Asp Leu Ala Ser
            755                 760                 765

Cys Lys Ser Pro Glu Tyr Asp Thr Val Phe Glu Asp Ser Ser Ser Ser
770                 775                 780

Ser Gly Glu Ser Ser Phe Leu Pro Glu Glu Glu Glu Glu Gly Glu
785                 790                 795                 800

Glu Glu Glu Glu Asp Asp Glu Glu Asp Ser Gly Val Ser Pro Thr
                805                 810                 815

Cys Ser Asp His Cys Pro Tyr Gln Ser Pro Ser Lys Ala Asn Arg
                820                 825                 830

Gln Leu Cys Ser Arg Ser Arg Ser Ser Gly Ser Ser Pro Cys His
                835                 840                 845

Ser Trp Ser Pro Ala Thr Arg Arg Asn Phe Arg Cys Glu Ser Arg Gly
        850                 855                 860

Pro Cys Ser Asp Arg Thr Pro Ser Ile Arg His Ala Arg Lys Arg Arg
865                 870                 875                 880

Glu Lys Ala Ile Gly Glu Gly Arg Val Val Tyr Ile Gln Asn Leu Ser
                885                 890                 895

Ser Asp Met Ser Ser Arg Glu Leu Lys Arg Arg Phe Glu Val Phe Gly
            900                 905                 910

Glu Ile Glu Glu Cys Glu Val Leu Thr Arg Asn Arg Arg Gly Glu Lys
        915                 920                 925

Tyr Gly Phe Ile Thr Tyr Arg Cys Ser Glu His Ala Ala Leu Ser Leu
        930                 935                 940

Thr Lys Gly Ala Ala Leu Arg Lys Arg Asn Glu Pro Ser Phe Gln Leu
945                 950                 955                 960

Ser Tyr Gly Gly Leu Arg His Phe Cys Trp Pro Arg Tyr Thr Asp Tyr
                965                 970                 975

Asp Ser Asn Ser Glu Glu Ala Leu Pro Ala Ser Gly Lys Ser Lys Tyr

```
                980             985             990
Glu Ala Met Asp Phe Asp Ser Leu Leu Lys Glu Ala Gln Gln Ser Leu
        995                     1000                1005
His
```